(12) United States Patent
Srinivasan et al.

(10) Patent No.: US 11,654,235 B2
(45) Date of Patent: May 23, 2023

(54) SENSOR CALIBRATION USING FABRICATION MEASUREMENTS

(71) Applicant: MEDTRONIC MINIMED, INC., Northridge, CA (US)

(72) Inventors: Akhil Srinivasan, Pacific Palisades, CA (US); Peter Ajemba, Canyon Country, CA (US); Steven C. Jacks, Culver City, CA (US); Robert C. Mucic, Glendale, CA (US); Tyler R. Wong, Pasadena, CA (US); Melissa Tsang, Sherman Oaks, CA (US); Chi-En Lin, Van Nuys, CA (US); Mohsen Askarinya, Chandler, AZ (US); David Probst, Chandler, AZ (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 842 days.

(21) Appl. No.: 16/569,401

(22) Filed: Sep. 12, 2019

(65) Prior Publication Data
US 2021/0077717 A1    Mar. 18, 2021

(51) Int. Cl.
*A61B 5/1495*    (2006.01)
*A61B 5/145*    (2006.01)
(Continued)

(52) U.S. Cl.
CPC ......... *A61M 5/1723* (2013.01); *A61B 5/1495* (2013.01); *A61B 5/14532* (2013.01);
(Continued)

(58) Field of Classification Search
CPC ............ A61M 5/1723; A61M 5/14244; A61M 2005/14208; A61M 2205/52;
(Continued)

(56) References Cited

U.S. PATENT DOCUMENTS

| 4,562,751 | A | 1/1986 | Nason et al. |
| 4,685,903 | A | 8/1987 | Cable et al. |

(Continued)

FOREIGN PATENT DOCUMENTS

| WO | 2005057168 A2 | 6/2005 |
| WO | 2006026741 A1 | 3/2006 |

OTHER PUBLICATIONS

U.S. Notice of Allowance dated Sep. 14, 2022 in U.S. Appl. No. 16/569,417.
(Continued)

*Primary Examiner* — Mohamed Charioui
(74) *Attorney, Agent, or Firm* — Weaver Austin Villeneuve & Sampson LLP

(57) ABSTRACT

Medical devices and related systems and methods are provided. A method of calibrating an instance of a sensing element involves obtaining fabrication process measurement data from a substrate having the instance of the sensing element fabricated thereon, obtaining a calibration model associated with the sensing element, determining calibration data associated with the instance of the sensing element for converting the electrical signals into a calibrated measurement parameter based on the fabrication process measurement data using the calibration model, and storing the calibration data in a data storage element associated with the instance of the sensing element.

20 Claims, 10 Drawing Sheets

(51) Int. Cl.
*A61M 5/172* (2006.01)
*A61M 5/142* (2006.01)
A61B 5/00 (2006.01)
G16H 20/17 (2018.01)

(52) U.S. Cl.
CPC ......... *A61M 5/14244* (2013.01); *A61B 5/145* (2013.01); *A61B 5/4839* (2013.01); *A61B 2560/0223* (2013.01); *A61B 2560/0228* (2013.01); *A61B 2560/0238* (2013.01); *A61M 2005/14208* (2013.01); *G16H 20/17* (2018.01)

(58) Field of Classification Search
CPC ....... A61B 5/14532; A61B 5/145; A61B 5/00; A61B 5/1495; A61B 5/4839; A61B 2560/0223; A61B 2560/02; A61B 2560/00; A61B 2560/0238; G16H 20/17; G16H 40/40
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,160,671 B2 * | 4/2012 | Kamath ............... A61B 5/7203 600/347 |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2011/0319734 A1 | 12/2011 | Gottlieb et al. |
| 2012/0103835 A1 * | 5/2012 | Liang .................. A61B 5/6849 204/403.01 |
| 2013/0338630 A1 | 12/2013 | Agrawal et al. |
| 2014/0066889 A1 | 3/2014 | Grosman et al. |
| 2015/0331418 A1 * | 11/2015 | Nogueira ............... G01D 18/00 702/104 |
| 2018/0169334 A1 | 6/2018 | Grosman et al. |
| 2021/0077718 A1 | 3/2021 | Jacks et al. |

OTHER PUBLICATIONS

U.S. Non-Final Office Action dated Jun. 8, 2022, in U.S. Appl. No. 16/569,417.

* cited by examiner

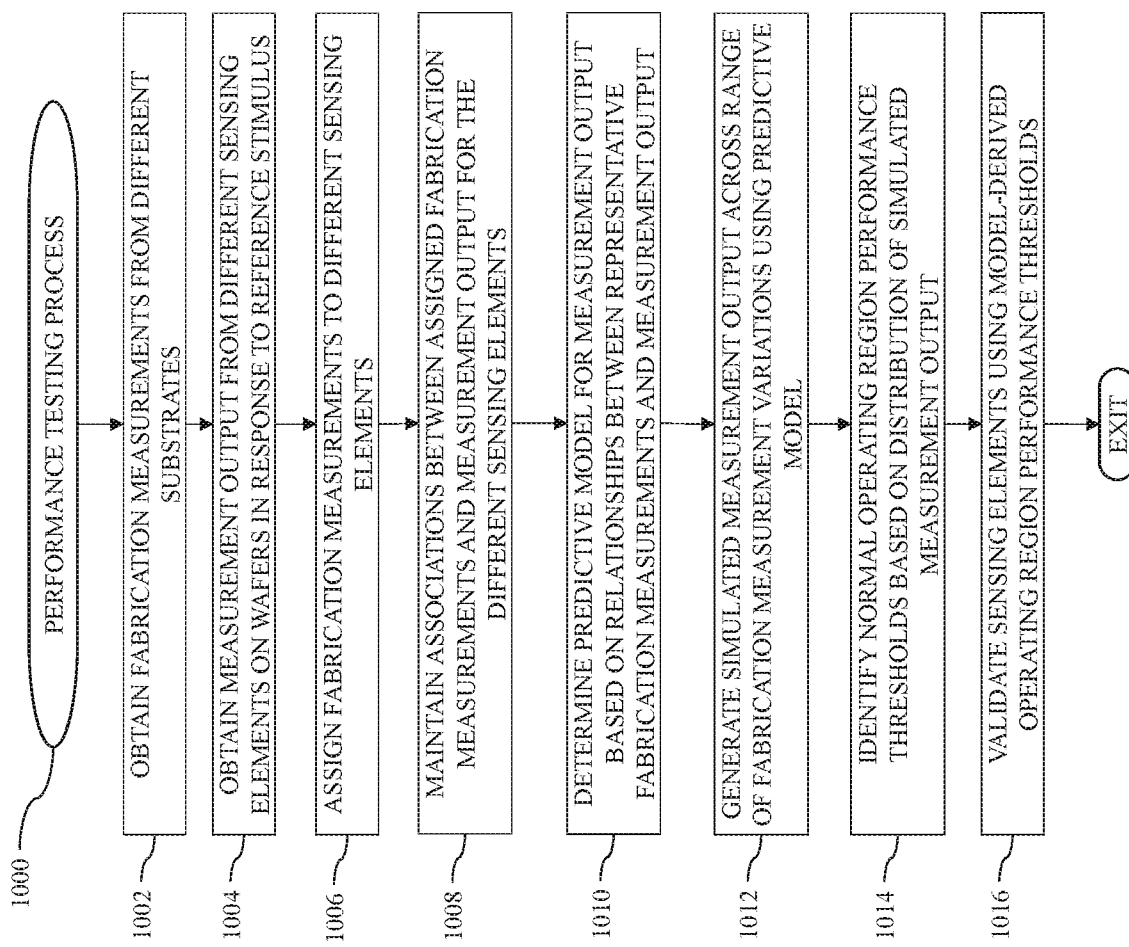

SENSOR CALIBRATION USING FABRICATION MEASUREMENTS

TECHNICAL FIELD

Embodiments of the subject matter described herein relate generally to medical devices, and more particularly, embodiments of the subject matter relate to calibrating sensing elements for use with medical devices.

BACKGROUND

Infusion pump devices and systems are relatively well known in the medical arts, for use in delivering or dispensing an agent, such as insulin or another prescribed medication, to a patient. Control schemes have been developed to allow insulin infusion pumps to monitor and regulate a patient's blood glucose level in a substantially continuous and autonomous manner. Rather than continuously sampling and monitoring a user's blood glucose level, which may compromise battery life, intermittently sensed glucose data samples are often utilized for purposes of continuous glucose monitoring (CGM) or determining operating commands for the infusion pump.

Many continuous glucose monitoring (CGM) sensors measure the glucose in the interstitial fluid (ISF). Typically, to achieve the desired level of accuracy and reliability and reduce the impact of noise and other spurious signals, the sensor data is calibrated using a known good blood glucose value, often obtained via a so-called "fingerstick measurement" using a blood glucose meters that measures the blood glucose in the capillaries. However, performing such calibration measurements increases the patient burden and perceived complexity, and can be inconvenient, uncomfortable, or otherwise disfavored by patients. Moreover, ISF glucose measurements lag behind the blood glucose measurements based on the time it takes glucose to diffuse from the capillary to the interstitial space where it is measured by the CGM sensor, which requires signal processing (e.g., filtering) or other techniques to compensate for physiological lag. Additionally, various factors can lead to transient changes in the sensor output, which may influence the accuracy of the calibration. Degradation of sensor performance over time or manufacturing variations may further compound these problems. Accordingly, it is desirable to provide sensor calibration in a manner that decreases the patient burden and improves the overall user experience without compromising accuracy or reliability.

BRIEF SUMMARY

Medical devices and related systems and operating methods are provided. An embodiment of a method of calibrating an instance of a sensing element capable of providing electrical signals influenced by a physiological condition in a body of a user is provided. The method involves obtaining fabrication process measurement data from a substrate having the instance of the sensing element fabricated thereon, obtaining a calibration model associated with the sensing element, determining calibration data associated with the instance of the sensing element for converting the electrical signals into a calibrated measurement parameter based on the fabrication process measurement data using the calibration model, and storing the calibration data in a data storage element associated with the instance of the sensing element.

In another embodiment, a method of operating a sensing arrangement is provided. The method involves obtaining, by a control module of the sensing arrangement, one or more electrical signals from a sensing element of the sensing arrangement, wherein the one or more electrical signals are influenced by a physiological condition in a body of a user, obtaining, by the control module, calibration data associated with the sensing element from a data storage element of the sensing arrangement, determining, by the control module, a calibrated measurement parameter based on the one or more measurement signals using the calibration data, obtaining a performance model associated with the sensing element, obtaining personal data associated with the patient, and determining a calibrated output value indicative of the physical condition based on the personal data and the calibrated measurement parameter using the performance model.

In another embodiment, a method of calibrating an interstitial glucose sensing element is provided. The method involves obtaining fabrication process measurement data from a substrate having the instance of the interstitial glucose sensing element fabricated thereon, obtaining a calibration model associated with the interstitial glucose sensing element, determining a calibration factor associated with the instance of the interstitial glucose sensing element for converting uncalibrated values for measurement parameter determined based on output signals from the interstitial glucose sensing element into a calibrated value based on the fabrication process measurement data using the calibration model, and storing the calibration factor in a data storage element associated with the instance of the sensing element.

In yet another embodiment, a method of manufacturing an instance of a sensing element capable of providing electrical signals influenced by a physiological condition in a body of a user is provided. The method involves obtaining fabrication process measurement data for a plurality of instances of the sensing element, obtaining reference output measurement data from the plurality of instances of the sensing element in response to a reference stimulus, determining a predictive model for a measurement output of the sensing element as a function of fabrication process measurement variables based on the relationship between the fabrication process measurement data and the reference output measurement data, generating a simulated output measurement distribution across a range of the fabrication process measurement variables using the predictive model, identifying performance thresholds for the measurement output based on the simulated output measurement distribution, obtaining output measurement data from the instance of the sensing element in response to the reference stimulus, and verifying the output measurement data satisfies the performance threshold prior to calibrating the instance of the sensing element.

In another embodiment, a method of calibrating an instance of a sensing element capable of providing electrical signals influenced by a physiological condition in a body of a user is provided. The method involves obtaining performance thresholds associated with a response of the sensing element to a reference stimulus, wherein the performance thresholds are derived using a predictive model for a measurement output of the sensing element as a function of fabrication process measurement variables, obtaining a current value for the measurement output from the instance of the sensing element in response to the reference stimulus, and after verifying the current value is within the performance thresholds, obtaining fabrication process measurement data associated with the instance of the sensing element, obtaining a calibration model associated with the sensing element, determining calibration data associated with the instance of the sensing element for converting the electrical signals into a calibrated measurement parameter based on the fabrication process measurement data using the calibration model, and storing the calibration data in a data storage element associated with the instance of the sensing element.

In yet another embodiment, a testing system is provided. The testing system includes a data storage element to maintain performance thresholds associated with a response of a sensing element to a reference stimulus, wherein the performance thresholds are derived using a predictive model for a measurement output of the sensing element as a function of fabrication process measurement variables and a processing system coupled to the data storage element to obtain output measurement data from an instance of the sensing element in response to the reference stimulus and verify the output measurement data satisfies the performance thresholds prior to calibration of the instance of the sensing element in accordance with a calibration model.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIG. 10 is a flow diagram of an exemplary sensor initialization process suitable for use with the sensing arrangement of FIG. 2 in conjunction with one or more of the processes of FIGS. 5-8 in one or more exemplary embodiments.

DETAILED DESCRIPTION

Figure 1:
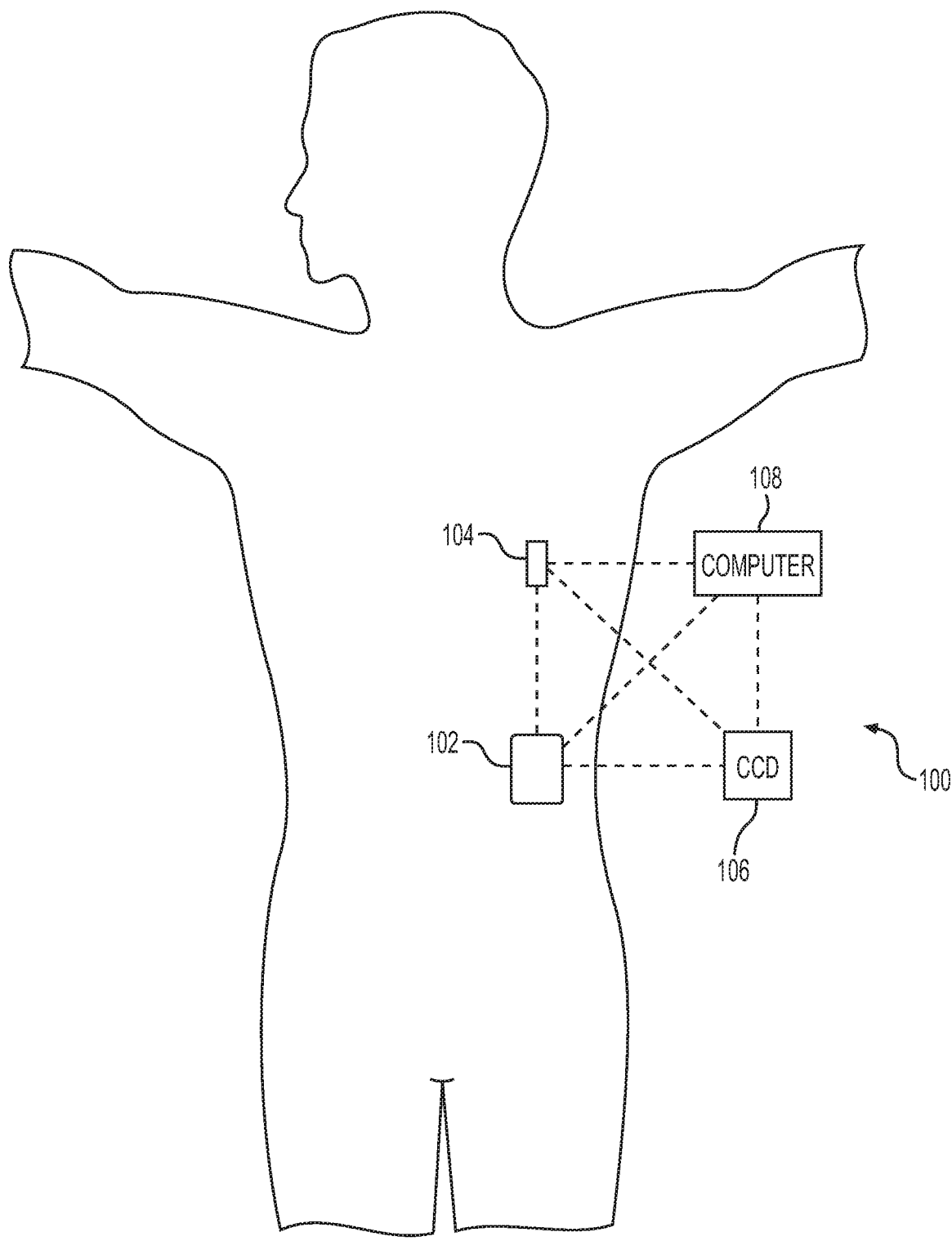
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein generally relate to calibrating sensing elements and related sensing arrangements and devices that provide an output that is indicative of and/or influenced by one or more characteristics or conditions that are sensed, measured, detected, or otherwise quantified by the sensing element. While the subject matter described herein is not necessarily limited to any particular type of sensing application, exemplary embodiments are described herein primarily in the context of a sensing element that generates or otherwise provides electrical signals indicative of and/or influenced by a physiological condition in a body of a human user or patient, such as, for example, interstitial glucose sensing elements.

As described in greater detail below, fabrication process measurement data associated with an instance of a sensing element is utilized to determine calibration data for converting electrical signals output by that instance of the sensing element into one or more calibrated measurement parameters based on a calibration model associated with the sensing element. In this regard, the calibration model maps one or more fabrication process measurements corresponding to the area or region of the substrate where a particular instance of the sensing element was manufactured to calibration factors for determining one or more calibration measurement parameters for the current instance of the sensing element. In exemplary embodiments, the calibration data is determined and stored or otherwise maintained in association with the instance of the sensing element after fabrication but prior to deployment of the sensing element. Thereafter, during operation, the calibration data may be utilized to convert electrical signals output by that instance of the sensing element into one or more calibrated measurement parameters. In exemplary embodiments, a performance model associated with the sensing element is utilized to convert the calibrated measurement parameters into a calibrated output value indicative of the sensed physiological condition of the patient using personal data associated with the patient or other data characterizing the nature or manner of operation of the sensing element. In this manner, calibrated measurement values for the physiological condition of the patient may be obtained without requiring a so-called "fingerstick measurement" or other reference measurements.

For purposes of explanation, exemplary embodiments of the subject matter are described herein as being implemented in conjunction with medical devices, such as portable electronic medical devices. Although many different applications are possible, the following description may focus on embodiments that incorporate a fluid infusion device (or infusion pump) as part of an infusion system deployment. That said, the subject matter may be implemented in an equivalent manner in the context of other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication. In this regard, the subject matter is not limited to medical applications and could be implemented in any device or application that includes or incorporates a sensing element.

Infusion System Overview

FIG. 1 depicts an exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the patient in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like. Generally, the fluid infusion device 102 includes a motor or other actuation arrangement that is operable to linearly displace a plunger (or stopper) of a reservoir provided within the fluid infusion device to deliver a dosage of fluid, such as insulin, to the body of a patient. Dosage commands that govern operation of the motor may be generated in an automated manner in accordance with the delivery control scheme associated with a particular operating mode, and the dosage commands may be generated in a manner that is influenced by a current (or most recent) measurement of the physiological condition in the body of the patient. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

The sensing arrangement 104 generally represents another medical device that includes the components of the infusion system 100 that are configured to sense, detect, measure or otherwise quantify a physiological condition of the patient, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the patient, and provide data indicative of the blood glucose level to the infusion device 102, the CCD 106 and/or the computer 108. For example, the infusion device 102, the CCD 106 and/or the computer 108 may include a display for presenting information or data to the patient based on the sensor data received from the sensing arrangement 104, such as, for example, a current glucose level of the patient, a graph or chart of the patient's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the patient based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108. While the subject matter is described herein in the context of glucose sensing, it should be appreciated the subject matter described herein is not necessarily limited to glucose sensing and may implemented in an equivalent manner for any number of other different enzymatic substances, such as, for example, lactate, beta-hydroxybutyrate, creatinine, etc.

Still referring to FIG. 1, in various embodiments, the sensing arrangement 104 may be secured to the body of the patient or embedded in the body of the patient at a location that is remote from the location at which the infusion device 102 is secured to the body of the patient. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the patient.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the patient that facilitates the patient's subsequent use of the infusion device 102. For example, the CCD 106 may provide information to the patient to allow the patient to determine the rate or dose of medication to be administered into the patient's body. In other embodiments, the CCD 106 may provide information to the infusion device 102 to autonomously control the rate or dose of medication administered into the body of the patient. In some embodiments, the sensing arrangement 104 may be integrated into the CCD 106. Such embodiments may allow the patient to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the patient without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the patient. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the patient, such as, blood glucose level or the like. The infusion device 102 is configured to deliver fluid in response to the condition sensed by the sensing arrangement 104. In turn, the sensing arrangement 104 continues to sense or otherwise quantify a current condition of the patient, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the patient is asleep or awake.

Figure 2:
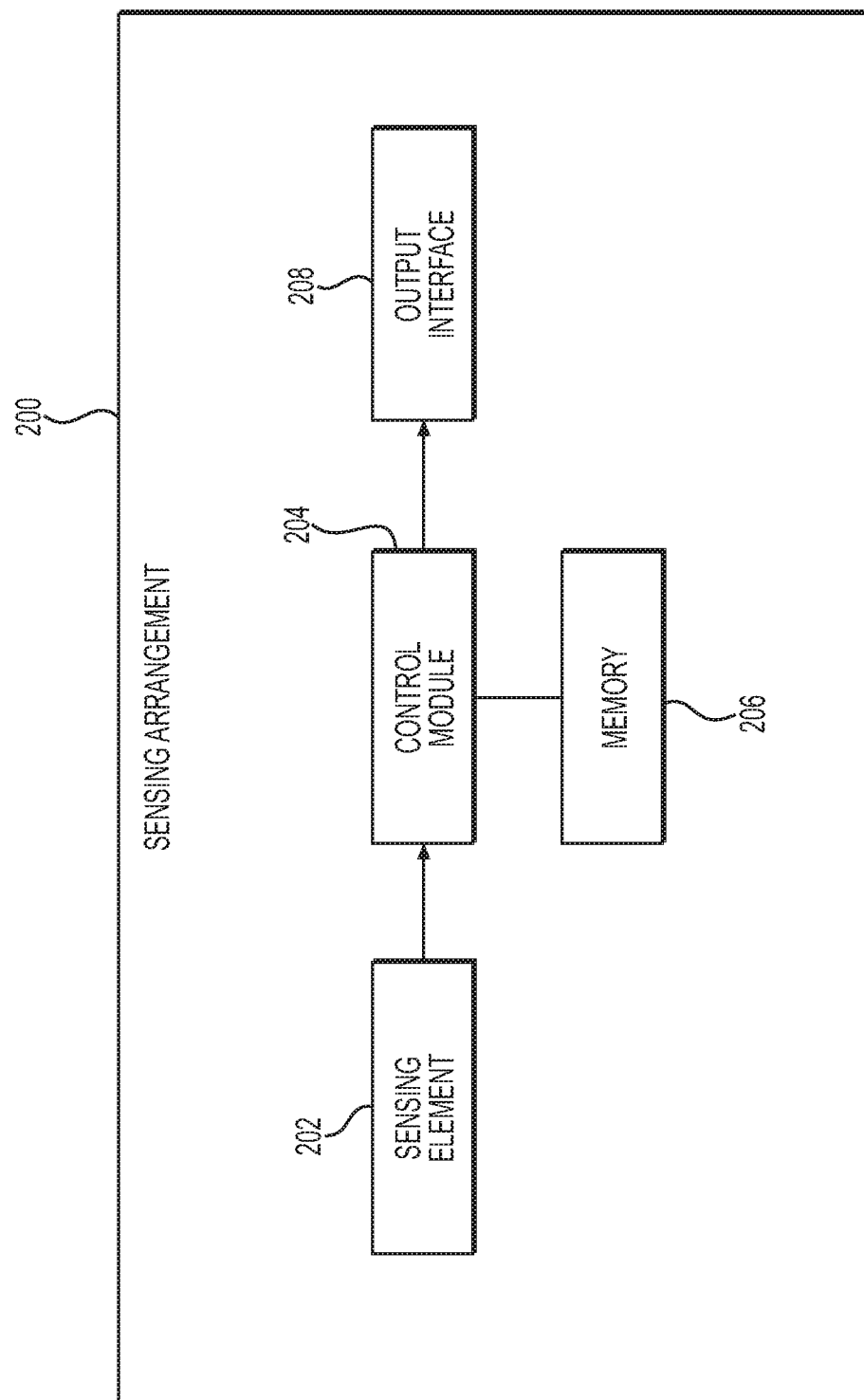
FIG. 2 is a block diagram of an exemplary embodiment of a sensing arrangement suitable for use in the infusion system of FIG. 1.

FIG. 2 depicts an exemplary embodiment of a sensing arrangement 200 suitable for use as the sensing arrangement 104 in the infusion system of FIG. 1 in accordance with one or more embodiments. The illustrated sensing device 200 includes, without limitation, a control module 204, a sensing element 202, an output interface 208, and a data storage element (or memory) 208. The control module 204 is coupled to the sensing element 202, the output interface 208, and the memory 206, and the control module 204 is suitably configured to support the operations, tasks, and/or processes described herein.

The sensing element 202 generally represents the component of the sensing device 200 that is configured to generate, produce, or otherwise output one or more electrical signals indicative of a condition that is sensed, measured, or otherwise quantified by the sensing device 200. In this regard, the physiological condition of a user influences a characteristic of the electrical signal output by the sensing element 202, such that the characteristic of the output signal corresponds to or is otherwise correlative to the physiological condition that the sensing element 202 is sensitive to. The sensing element 202 may be realized as a glucose sensing element that generates an output electrical signal having a current (or voltage) associated therewith that is correlative to the interstitial fluid glucose level that is sensed or otherwise measured in the body of the patient by the sensing arrangement 104, 200.

Still referring to FIG. 2, the control module 204 generally represents the hardware, circuitry, logic, firmware and/or other component(s) of the sensing device 200 that is coupled to the sensing element 202 to receive the electrical signals output by the sensing element 202 and perform various additional tasks, operations, functions and/or processes described herein. For example, the control module 204 may filter, analyze or otherwise process the electrical signals received from the sensing element 202 to obtain a measurement value for conversion into a calibrated measurement of the interstitial fluid glucose level. Additionally, in one or more embodiments, the control module 204 also implements or otherwise executes a calibration application module that calculates or otherwise determines calibrated measurement parameters based on the measurement value using calibration data associated with the sensing element 202 that is stored or otherwise maintained in the memory 206, as described in greater detail below. The calibrated measurement parameters may then be utilized to obtain a calibrated measurement value for the patient's interstitial glucose level, as described in greater detail below.

Depending on the embodiment, the control module 204 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 204, or in any practical combination thereof. In exemplary embodiments, the control module 204 includes or otherwise accesses the data storage element or memory 206. The memory 206 may be realized using any sort of RAM, ROM, flash memory, registers, hard disks, removable disks, magnetic or optical mass storage, short or long term storage media, or any other non-transitory computer-readable medium capable of storing programming instructions, code, or other data for execution by the control module 204. The computer-executable programming instructions, when read and executed by the control module 204, cause the control module 204 to perform the tasks, operations, functions, and processes described in greater detail below.

In some embodiments, the control module 204 includes an analog-to-digital converter (ADC) or another similar sampling arrangement that samples or otherwise converts the output electrical signal received from the sensing element 202 into corresponding digital measurement data value correlative to the interstitial fluid glucose level sensed by the sensing element 202. In other embodiments, the sensing element 202 may incorporate an ADC and output a digital measurement value. In one or more embodiments, the current of the electrical signal output by the sensing element 202 is influenced by the user's interstitial fluid glucose level, and the digital measurement data value is realized as a current measurement value provided by an ADC based on an analog electrical output signal from the sensing element 202.

The output interface 208 generally represents the hardware, circuitry, logic, firmware and/or other components of the sensing arrangement 200 that are coupled to the control module 204 for outputting data and/or information from/to the sensing device 200, for example, to/from the infusion device 102, the CCD 106 and/or the computer 108. In this regard, in exemplary embodiments, the output interface 208 is realized as a communications interface configured to support communications to/from the sensing device 200. In such embodiments, the communications interface 208 may include or otherwise be coupled to one or more transceiver modules capable of supporting wireless communications between the sensing device 200 and another electronic device (e.g., an infusion device 102 or another electronic device 106, 108 in an infusion system 100). Alternatively, the communications interface 208 may be realized as a port that is adapted to receive or otherwise be coupled to a wireless adapter that includes one or more transceiver modules and/or other components that support the operations of the sensing device 200 described herein. In other embodiments, the communications interface 208 may be configured to support wired communications to/from the sensing device 200. In yet other embodiments, the output interface 208 may include or otherwise be realized as an output user interface element, such as a display element (e.g., a light-emitting diode or the like), a display device (e.g., a liquid crystal display or the like), a speaker or another audio output device, a haptic feedback device, or the like, for providing notifications or other information to the user. In such embodiments, the output user interface 208 may be integrated with the sensing arrangement 104, 200 (e.g., within a common housing) or implemented separately.

It should be understood that FIG. 2 is a simplified representation of a sensing device 200 for purposes of explanation and is not intended to limit the subject matter described herein in any way. In this regard, although FIG. 2 depicts the various elements residing within the sensing device 200, one or more elements of the sensing device 200 may be distinct or otherwise separate from the other elements of the sensing device 200. For example, the sensing element 202 may be separate and/or physically distinct from the control module 204 and/or the communications interface 208. Furthermore, features and/or functionality of described herein as implemented by the control module 204 may alternatively be implemented at the infusion device 102 or another device 106, 108 within an infusion system 100.

Sensor Fabrication

Figure 3:
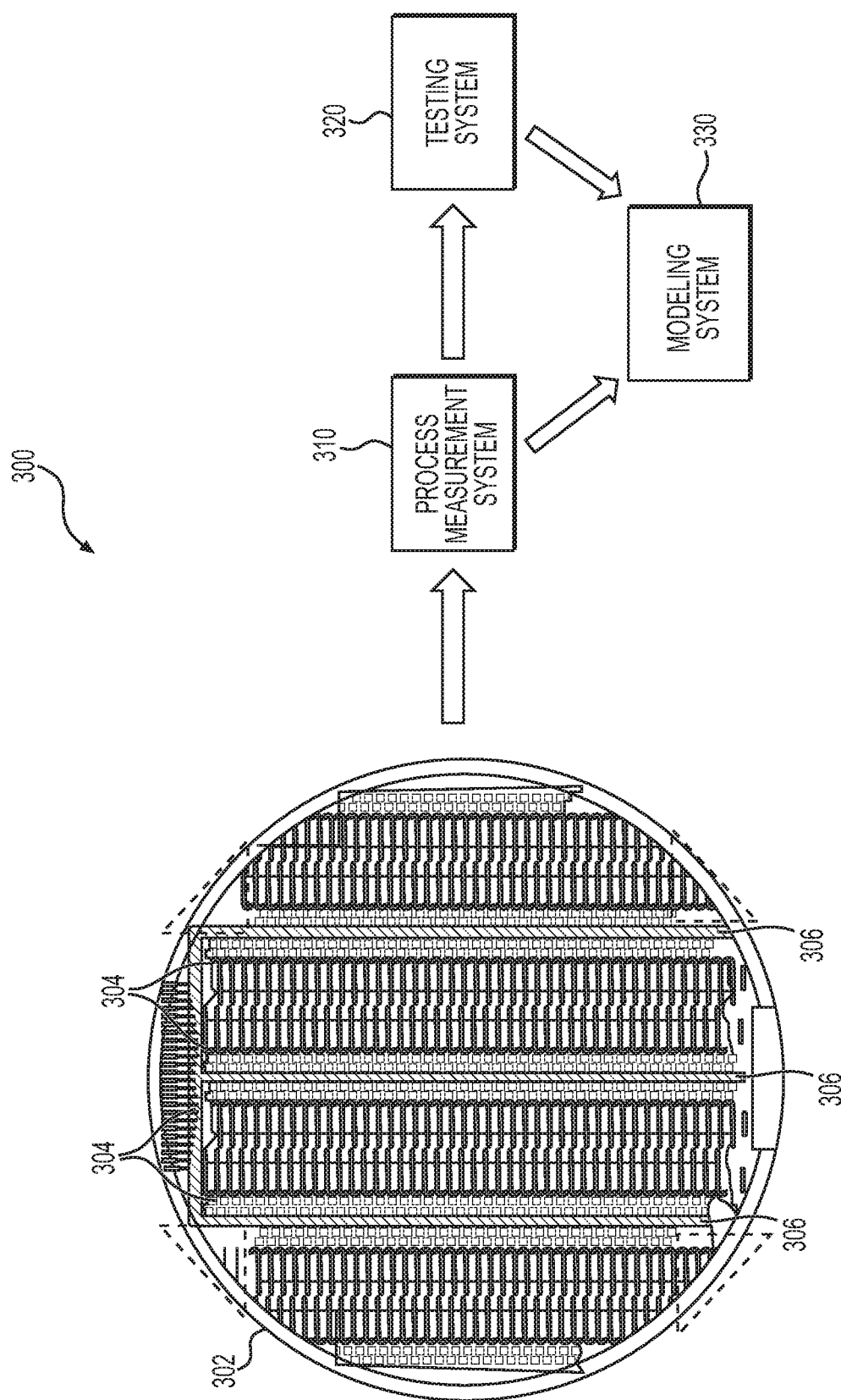
FIG. 3 depicts a fabrication system for fabricating and calibrating a sensing element suitable for use in the sensing arrangement of FIG. 2.

FIG. 3 depicts an exemplary embodiment of a fabrication system 300 for developing calibration models for sensing elements fabricated on a substrate 302. In this regard, multiple instances of a sensing element may be fabricated on a substrate 302, which is subsequently diced into smaller discrete portions (or dies) containing a respective instance of the sensing element. In exemplary embodiments, the different instances of electrochemical sensing elements are concurrently fabricated on or within regions 304 of the substrate 302, alternatively referred to herein as sensing regions, while process control monitors (PCM) are concurrently fabricated on or within other regions 306 of the substrate 302 that are adjacent to or otherwise in the vicinity of the sensing regions 304. For example, in the illustrated embodiments, the sensing regions 304 are arranged in vertically-oriented columns on the substrate 302 with the PCM regions 306 being realized as vertically-oriented columns interposed between neighboring sensing regions 304. In this regard, the PCM regions 306 may include multiple PCMs running vertically throughout the length of the PCM regions 306, while the sensing regions 304 include multiple instances of sensing elements running vertically throughout the length of the sensing regions 304.

After and/or during fabrication, the PCMs fabricated within the PCM regions 306 are analyzed using one or more process measurement systems 310 to obtain fabrication process measurements for each PCM fabricated on the substrate 302. In this regard, the process measurement system 310 is capable of measuring the biological, chemical, electrical, and/or physical characteristics of the respective PCMs. The fabrication process measurement data obtained for each PCM may include, for example, glucose oxidase (GOx) thickness, GOx activity, glucose limiting membrane (GLM) thickness, working electrode (WE) platinum imaginary impedance, counter electrode (CE) platinum imaginary impedance, and human serum albumin (HSA) concentration. That said, it should be noted that the subject matter described herein is not intended to be limited to any particular type or number of fabrication process measurements, and the fabrication process measurements could include measurements of any number of different properties or characteristics (e.g., dielectric characteristics, permeability, diffusivity, etc.). Additionally, or alternatively, in some embodiments, the fabrication process measurements may be obtained by directly measuring characteristics of the sensing elements on the sensing regions 304.

Figure 4:
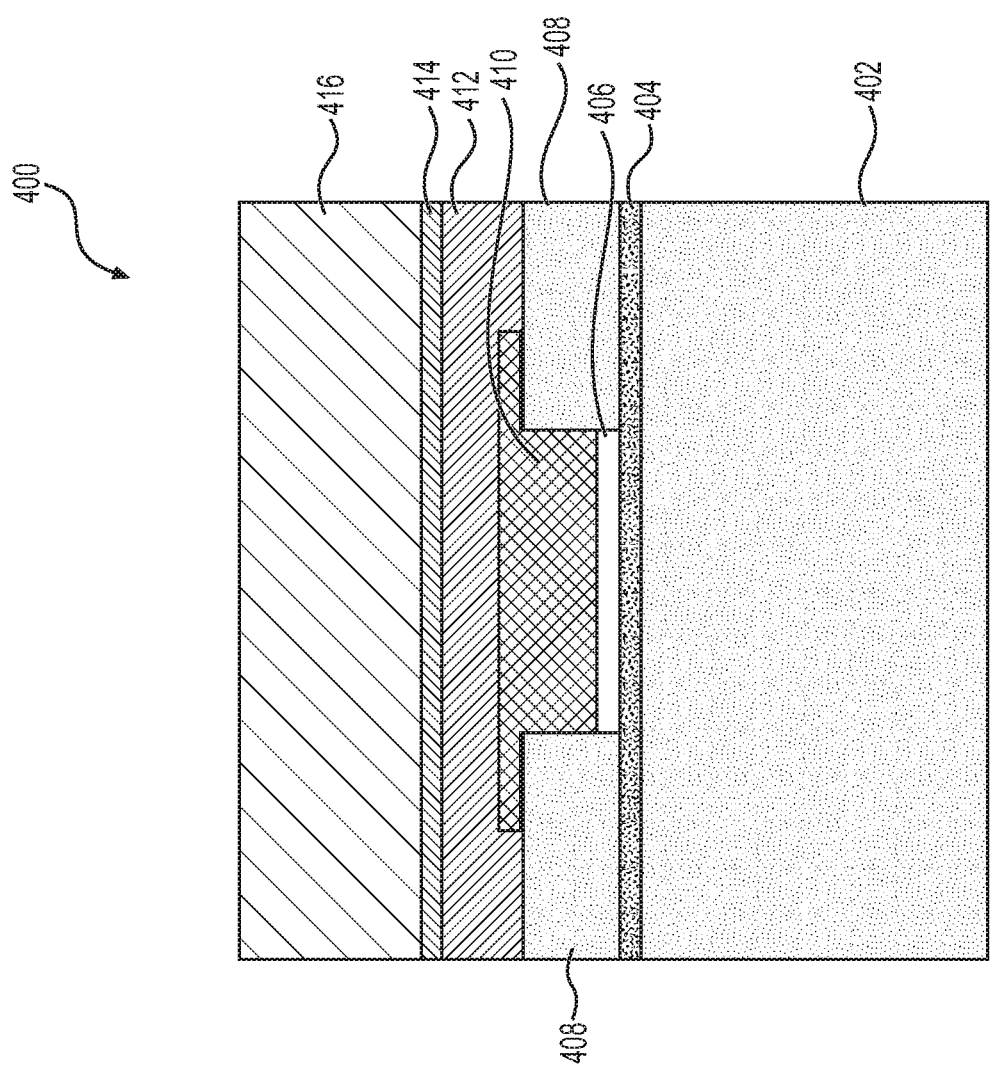
FIG. 4 is a cross-section of an electrode of an interstitial glucose sensing element suitable for fabrication by the fabrication system of FIG. 3 for use in the sensing arrangement of FIG. 2.

FIG. 4 depicts a cross-section of a working electrode 400 suitable for fabrication on the substrate 302 within sensing regions 304 for use in an interstitial glucose sensing element. Additionally, in some embodiments, dummy versions of the working electrode 400 may be fabricated within the PCM regions 306 for purposes of obtaining fabrication process measurements. The working electrode 400 includes a substrate or base layer 402 (e.g., polyimide) and an overlying plated metallic layer 404 (e.g., chromium and gold). An electroplated layer 406 (e.g., platinum) is provided on the metallic layer 404 between portions of an insulating layer 408 (e.g., polyimide). A glucose oxidase layer 410 is formed overlying the layer 406 by depositing a glucose oxidase solution (e.g., via slot coating), and a human serum albumin (HSA) layer 412 is formed overlying the glucose oxidase layer 410. An adhesive layer 414 is provided overlying the HSA layer 412 to affix a glucose limiting membrane (GLM) layer 416 overlying the working electrode 400. The counter electrode of the interstitial glucose sensing element may be similar or substantially identical to the working electrode 400 but lacking the glucose oxidase layer 410.

To obtain fabrication process measurements, in an exemplary embodiment, an imaginary impedance of the working electrode (and similarly, the imaginary impedance for the counter electrode) is measured after a platinum electroplating process to form layer 406. The GOx solution activity measurements may be acquired during or after the GOx solution preparation process prior to deposition, while the GOx thickness (e.g., the thickness of layer 410) is measured after the slot coating and selective patterning processes over the working electrode 400. The HSA concentration may be measured during or after the solution preparation process prior to spray coating the HSA layer 412 on the substrate, and the GLM thickness (e.g., the thickness of layer 416) may be measured prior to applying the GLM layer 416. In one or more embodiments, these measurements are performed with respect to sacrificial or monitor instances of the working electrode 400 fabricated within PCM regions 306 on the substrate 302. In some embodiments, additional fabrication process measurements such as surface roughness or other topographic measurements may be obtained for the working electrode 400 during or after fabrication (e.g., via interferometry).

It should be appreciated that FIG. 4 depicts a simplified representation of one exemplary embodiment of the working electrode 400, and practical embodiments may include any number of additional and/or alternative layers (e.g., a high-density amine (HDA) layer, etc.). Accordingly, the subject matter described herein is not intended to be limited to the embodiment depicted in FIG. 4.

Referring again to FIG. 3, the fabrication process measurements obtained by the process measurement system 310 are provided to a modeling system 330. In one or more embodiments, the modeling system 330 interpolates and/or extrapolates the fabrication process measurement data for different PCMs to obtain representative fabrication process measurement data for a given instance of a sensing element fabricated on the substrate 302. In this regard, the modeling system 330 may maintain an association between the location of a respective PCM on the substrate 302 (e.g., a coordinate location) and the corresponding fabrication process measurements obtained for that respective PCM. Thereafter, based on the location of a respective sensing element fabricated on the substrate 302, the modeling system 330 may identify the subset of PCMs that are neighboring, adjacent, or otherwise proximate to that respective sensing element, obtain the fabrication process measurement data for the identified subset of PCMs, and then average or otherwise combine the fabrication process measurement data for the different PCMs of the subset based on the relationship between the location of the respective sensing element relative to the locations of the different PCMs to obtain representative fabrication process measurement data for the location on the substrate 302 corresponding to where the respective sensing element was fabricated.

In exemplary embodiments, each of the different sensing elements fabricated within the sensing regions 304 are analyzed using one or more testing systems 320 to obtain reference measurement outputs for each sensing element fabricated on the substrate 302 in response to one or more known reference inputs. For example, in exemplary embodiments, the sensing elements fabricated within the sensing regions 304 are realized as electrochemical interstitial glucose sensing elements that are exposed to known concentrations of glucose, with the testing system 320 including glucose sensor transmitters, recorders, ammeters, voltmeters, or suitable measuring instruments capable of measuring characteristics of the resulting output signals that are generated or otherwise provided by the glucose sensing elements. In this regard, the reference output measurement parameters obtained for each sensing element may include one or more of the electrical current output by the sensing element in response to a reference glucose concentration, electrochemical impedance spectroscopy (EIS) values (for one or more frequencies) or other measurements indicative of a characteristic impedance associated with the sensing element in response to a reference glucose concentration, counter electrode voltage (Vctr) (e.g., the difference between counter electrode potential and working electrode potential), and the like. For example, a glucose sensor transmitter may include potentiostat hardware and firmware cooperatively configured to collect electrical current measurements corresponding to the electrical current through the working electrode resulting from an applied bias potential and reaction of the glucose oxidase layer(s) of the working electrode of the sensing element to a reference glucose concentration, while also calculating the counter electrode voltage (Vctr) by difference of the measured counter electrode potential and working electrode potential. The glucose sensor transmitter may also be configured to perform electrochemical impedance spectroscopy at various time intervals and at multiple frequencies with respect to the electrical current and voltage at the working electrode.

The reference output measurement parameters obtained by the testing system 320 are provided to the modeling system 330, which maintains the reference output measurement parameters in association with the respective instance of a sensing element fabricated on the substrate 302. In this regard, the modeling system 330 maintains an association between the reference output measurement parameters for a respective sensing element fabricated on the substrate 302 and the representative fabrication process measurements for that respective sensing element fabricated on the substrate 302. As described in greater detail below, based on the relationships between the fabrication process measurement data and the reference measurement output data for the various different instances of a sensing element, the modeling system 330 determines calibration models for calculating or otherwise predicting output measurement parameters for a sensing element as a function of one or more fabrication process measurement parameters associated with that sensing element. In this regard, the output measurement parameters determined using the calibration models are effectively calibrated to account for fabrication process variations, and accordingly, are alternatively referred to herein as calibrated measurement parameters.

Manufacturing Calibration

Figure 5:
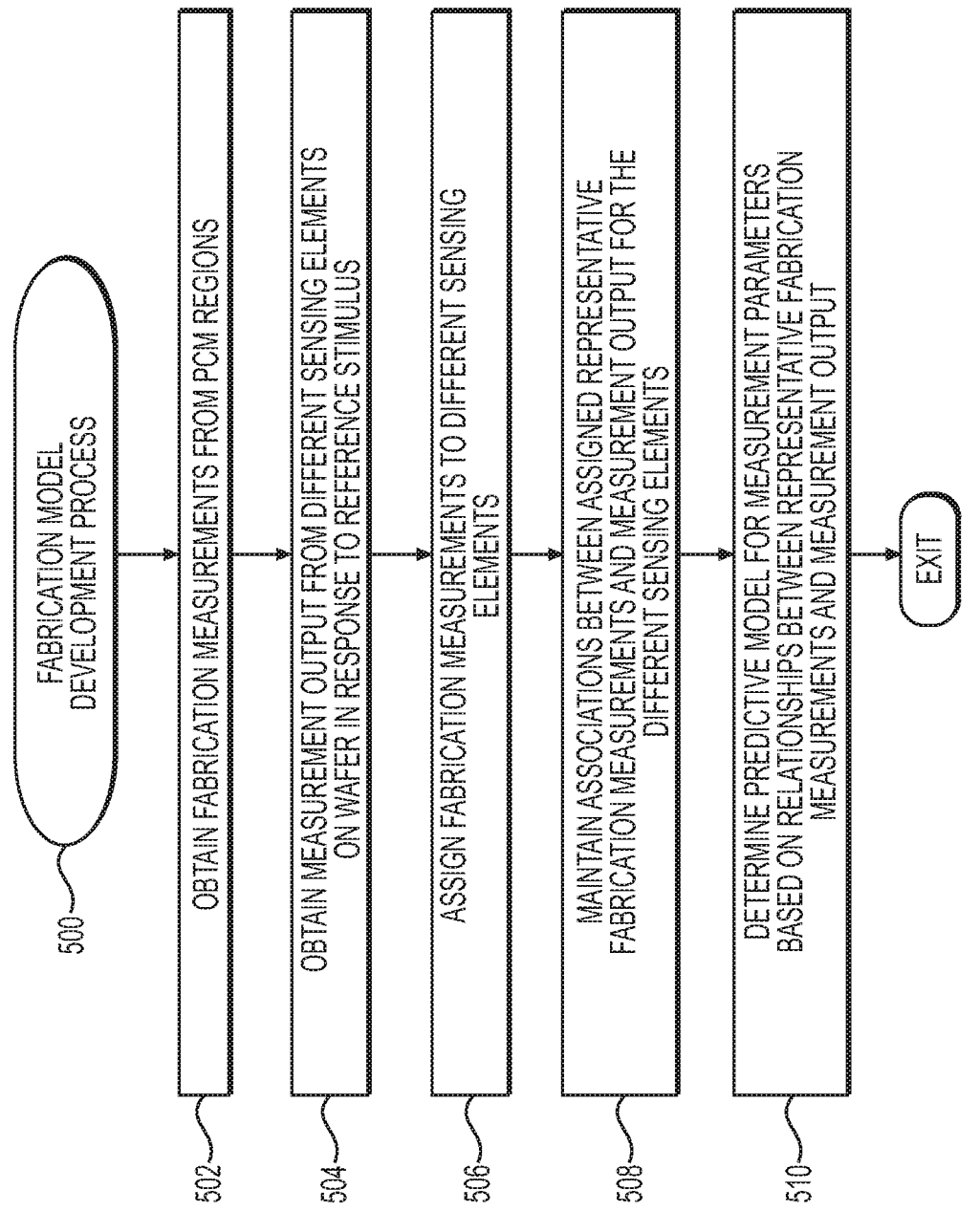
FIG. 5 is a flow diagram of an exemplary fabrication model development process suitable for use with the fabrication system of FIG. 3 in one or more exemplary embodiments.

FIG. 5 depicts an exemplary embodiment of a fabrication model development process 500 for developing calibration models that map fabrication process measurements for a sensing element to corresponding calibration measurement parameters for that sensing element. The various tasks performed in connection with the fabrication model development process 500 may be performed by hardware, firmware, software executed by processing circuitry, or any combination thereof. For illustrative purposes, the following description may refer to elements mentioned above in connection with FIGS. 1-3. It should be appreciated that the fabrication model development process 500 may include any number of additional or alternative tasks, the tasks need not be performed in the illustrated order and/or the tasks may be performed concurrently, and/or the fabrication model development process 500 may be incorporated into a more comprehensive procedure or process having additional functionality not described in detail herein. Moreover, one or more of the tasks shown and described in the context of FIG. 5 could be omitted from a practical embodiment of the fabrication model development process 500 as long as the intended overall functionality remains intact.

The illustrated fabrication model development process 500 begins by receiving or otherwise obtaining fabrication process measurements from different PCM regions on a substrate having sensing elements fabricated thereon (task 502). For example, as described above, the process measurement system 310 analyzes the PCM regions 306 on the substrate 302 to obtain, for each PCM region 306, one or more measurements of the physical characteristics of the respective PCM region 306. The measurements of the physical characteristics of the PCM regions 306 are provided to the modeling system 330 which maintains associations between the respective measurements and the respective locations of the respective PCM regions 306 on the substrate 302. The fabrication model development process 500 also receives or otherwise obtains measurement signal outputs from the different sensing elements fabricated on the substrate (task 504). For example, as described above, the testing system 320 tests or otherwise analyzes the different sensing elements 304 fabricated on the substrate 302 to obtain, for each sensing element 304, one or more reference measurement outputs generated or otherwise provided by the respective sensing element 304 in response to one or more known reference inputs. The reference measurement outputs are provided to the modeling system 330 which maintains associations between the respective reference measurement outputs and the respective locations of the respective sensing elements 304 on the substrate 302.

In the illustrated embodiment, the fabrication model development process 500 continues by assigning fabrication process measurements to each of the sensing elements fabricated on the substrate and maintaining associations between the assigned fabrication process measurements and reference measurement outputs for each sensing element (tasks 506, 508). For example, as described above, using the coordinate location for where a respective sensing element 304 was fabricated on the substrate 302, the modeling system 330 may calculate or otherwise determine estimated fabrication process measurements for that coordinate location based on fabrication process measurements from different PCM regions 306 around that coordinate location. In this regard, interpolation techniques (e.g., multivariate interpolation) may be employed to derive an estimate of what the physical characteristics of the respective sensing element 304 are likely to be based on fabrication process measurements associated with neighboring PCM regions 306 in a manner that accounts for the spatial relationships between the coordinate location of the sensing element 304 relative to the respective coordinate locations of the neighboring PCM regions 306. For each respective sensing element 304, the modeling system 330 may maintain an association between the representative or estimated fabrication process measurements assigned to the respective sensing element 304, the reference measurement outputs obtained from that respective sensing element 304, and coordinate location on the substrate 302 where that respective sensing element 304 was fabricated. Additionally, or alternatively, some embodiments may obtain fabrication process measurements directly from the respective sensing element 304, which, may be utilized individually or in combination with estimated fabrication process measurements derived from the PCM regions 306. Accordingly, the subject matter described herein is not necessarily limited to any particular location from which the fabrication process measurements are obtained.

Still referring to FIG. 5, the fabrication model development process 500 utilizes the relationships between the reference measurement outputs and fabrication process measurements for different sensing elements to calculate or otherwise determine a predictive model for determining calibrated measurement parameters as a function of the fabrication process measurements (task 510). In this regard, for each different measurement parameter, the modeling system 330 may utilize machine learning or artificial intelligence techniques to determine which combination of fabrication process measurement parameters are correlated to or predictive of the respective calibration measurement parameter, and then determine a corresponding equation, function, or model for calculating a calibration factor (or scaling factor) for determining an effectively calibrated value of the parameter of interest based on that set of input variables. Thus, the model is capable of characterizing or mapping a particular combination of one or more fabrication process measurement parameters to a calibration factor for determining an effectively calibrated value for the calibration parameter of interest (e.g., electrical current output, EIS value, or the like).

For example, an interstitial sensing element may be designed to produce a particular amount of current in response to the reference glucose concentration utilized by the testing system 320, alternatively referred to herein as the design current. For each sensing element, the modeling system 330 may divide the measured reference electrical current output for the respective sensing element in response to the reference glucose concentration by the design current to determine an output electrical current calibration factor for each sensing element. Thereafter, the modeling system 330 may utilize machine learning to identify which combination of fabrication process measurement parameters are correlated to or predictive of the output electrical current calibration factors, and then determine a corresponding equation, function, or model for calculating the output electrical current calibration factor based on that subset of fabrication process measurement input variables. Similarly, measured reference EIS values for the respective sensing elements may be divided by a design EIS value to determine EIS calibration factor for each sensing element, which, in turn, are utilized to determine a corresponding equation, function, or model for calculating an EIS calibration factor based on a subset of correlative fabrication process measurement input variables.

As another example, a neural network model may be developed using linear regression and an appropriate activation function, which could vary depending on the calibration parameter of interest. The fabrication measurement inputs and calibration parameter outputs are structured into corresponding matrices or vectors, which are then fed into a loss function with initial values for cost, weights, and bias for mapping the input matrix to the output matrix. The initial values are then input into the linear equation and activation portions of the neuron to initialize the neural network. The cost is then computed and a gradient descent performed to determine updated weights and an updated bias as a result of the gradient descent and an optimized characteristic learning rate. The process is then iteratively repeated for a desired number of iterations (e.g., 1000 iterations) to "learn" the weights and bias to be utilized as part of the predictive model for the calibration parameter(s).

It should be noted that the subset of fabrication process measurement parameters that are predictive of or correlative for a particular calibration measurement parameter may vary from other calibration measurement parameters. Additionally, the relative weightings applied to the respective fabrication measurement parameters of that predictive subset may also vary from other calibration measurement parameters who may have common predictive subsets, based on differing correlations between a particular fabrication measurement variable and the reference measurement data for that calibration parameter. In this regard, each measurement has a specific weight depending on the degree of influence (or lack thereof) with respect to the particular measurement parameter. For example, the electrical current output may be most strongly correlated to the GLM thickness and GOx thickness. It should also be noted that any number of different machine learning techniques may be utilized to determine what fabrication process measurement parameters are predictive for a calibration measurement parameter of interest, such as, for example, genetic programming, support vector machines, Bayesian networks, probabilistic machine learning models, or other Bayesian techniques, fuzzy logic, heuristically derived combinations, or the like. Additionally, in practice, prior to model development, the preceding tasks 502, 504, 506, 508 of the fabrication model development process 500 may be performed multiple times for multiple different substrates until a sufficient number of sensing elements and corresponding data sets have been obtained to achieve the desired level of accuracy or reliability for the resulting models.

Figure 6:
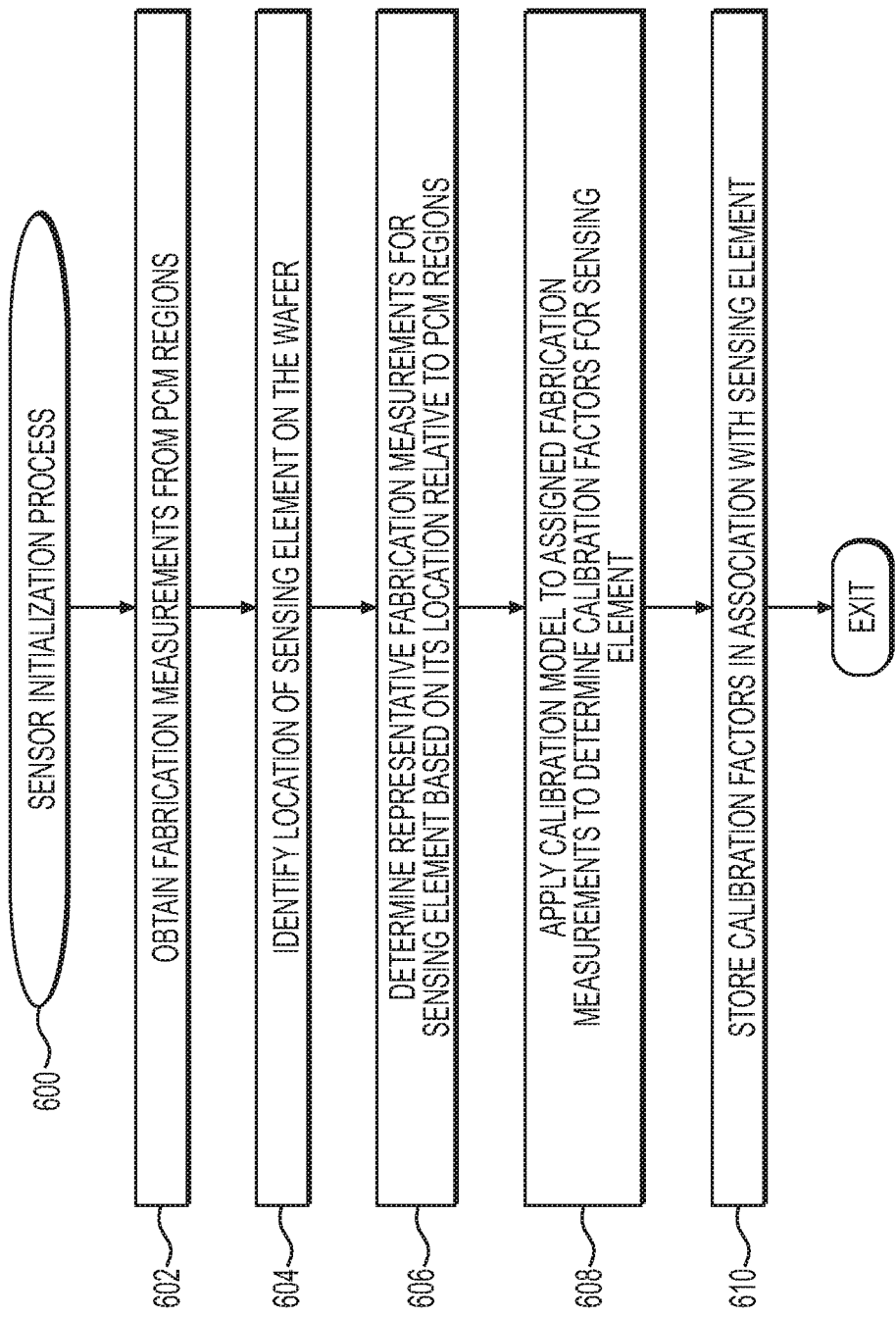
FIG. 6 is a flow diagram of an exemplary sensor initialization process suitable for use with the sensing arrangement of FIG. 2 in conjunction with the fabrication model development process of FIG. 5 in one or more exemplary embodiments.

FIG. 6 depicts an exemplary embodiment of a sensor initialization process 600 for utilizing calibration models from the fabrication model development process 500 to configure sensing elements after fabrication and prior to deployment. The various tasks performed in connection with the sensor initialization process 600 may be performed by hardware, firmware, software executed by processing circuitry, or any combination thereof. For illustrative purposes, the following description may refer to elements mentioned above in connection with FIGS. 1-3. It should be appreciated that the sensor initialization process 600 may include any number of additional or alternative tasks, the tasks need not be performed in the illustrated order and/or the tasks may be performed concurrently, and/or the sensor initialization process 600 may be incorporated into a more comprehensive procedure or process having additional functionality not described in detail herein. Moreover, one or more of the tasks shown and described in the context of FIG. 6 could be omitted from a practical embodiment of the sensor initialization process 600 as long as the intended overall functionality remains intact.

In exemplary embodiments, the sensor initialization process 600 is performed with respect to sensing elements fabricated after calibration models have been developed to allow calibration factors or scaling factors to be assigned to the sensing elements based on fabrication process measurement data without requiring testing to empirically determine calibration data for a respective sensing element. Similar to the fabrication model development process 500, the sensor initialization process 600 begins by receiving or otherwise obtaining fabrication process measurements from different PCM regions on a substrate having sensing elements fabricated thereon, identifying the location of the respective sensing element on the substrate, and determining representative fabrication process measurement data for the respective sensing element based on its location (tasks 602, 604, 606). As described above, the substrate 302 is provided to a process measurement system 310 for measuring physical characteristics of different PCM regions 306 on the substrate 302. Based on the coordinate location where a respective sensing element was fabricated, estimated fabrication process measurements for the sensing element are calculated or otherwise determined based on the respective sensing element's spatial relationship with respect to neighboring PCM regions 306, for example, by a multivariate interpolation of the fabrication process measurements associated with the neighboring PCM regions 306.

After obtaining the fabrication process measurement parameters for the current instance of the sensing element of interest, the sensor initialization process 600 continues by applying the calibration models developed for that sensing element to the estimated fabrication process measurements to determine calibration factors or scaling factors for the current instance of the sensing element (task 608). In this regard, for each respective calibration measurement parameter, the correlative subset of the estimated fabrication process measurements for that respective calibration measurement parameter are input or otherwise provided to the calibration model for that respective calibration measurement parameter to calculate a corresponding calibration factor for converting output from the sensing element into a calibrated value for that respective calibration measurement parameter. Thus, for an interstitial glucose sensing element, a first calibration factor may be determined for converting the electrical current output from the interstitial glucose sensing element into a calibrated electrical current output, a second calibration factor may be determined for converting an EIS value into a calibrated EIS value, and so on.

After determining the calibration factors for the different calibration measurement parameters, the sensor initialization process 600 continues by storing or otherwise maintaining the calibration data in association with the sensing element (task 610). In this regard, in exemplary embodiments, for each respective calibration measurement parameter, a corresponding calibration factor is stored or otherwise maintained in the memory 206 of the sensing arrangement 200 that includes the respective sensing element 202. Thereafter, when the sensing arrangement 200 is in use, the control module 204 utilizes the stored calibration factors in the memory 206 to convert the different measured values for the calibration measurement parameters determined based on the output of the sensing element 202 (e.g., the electrical current output, EIS values, and the like) into calibrated values. For example, the control module 204 may determine a raw or uncalibrated EIS value based on the output signals provided by the sensing element 202 and then multiply or otherwise convert the EIS value into a calibrated EIS value using the model-derived EIS calibration factor stored in the memory 206. In this manner, the sensing arrangement 200 may be configured to output measurement parameter values that are effectively calibrated account for fabrication process variations without requiring testing of the sensing element 202.

Figure 7:
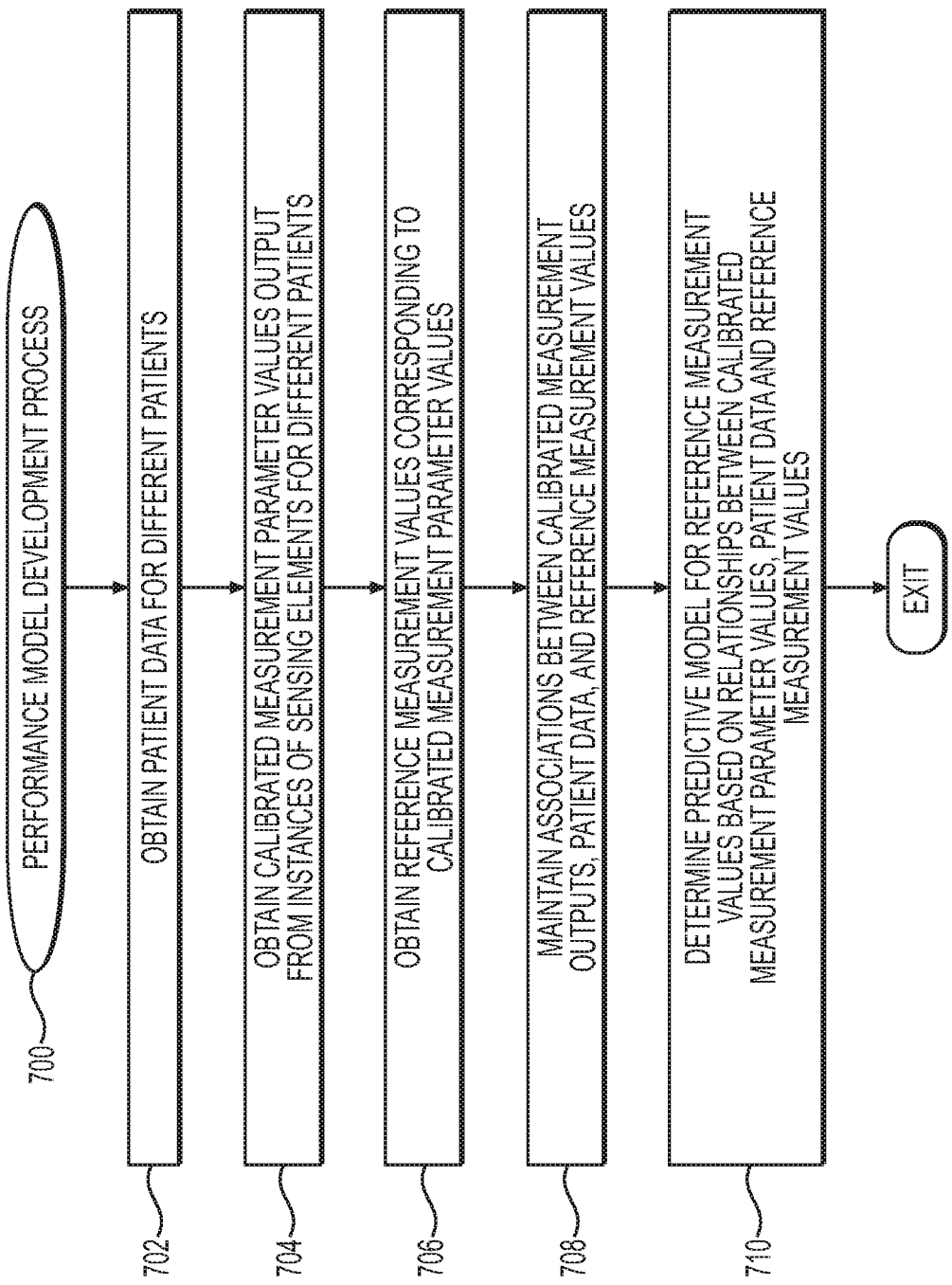
FIG. 7 is a flow diagram of an exemplary performance model development process suitable for use with a sensing arrangement in one or more exemplary embodiments.

FIG. 7 depicts an exemplary embodiment of a performance model development process 700 for developing one or more models that map calibration measurement parameters provided by a sensing device into a calibrated measurement value. The various tasks performed in connection with the performance model development process 700 may be performed by hardware, firmware, software executed by processing circuitry, or any combination thereof. For illustrative purposes, the following description may refer to elements mentioned above in connection with FIGS. 1-3. It should be appreciated that the performance model development process 700 may include any number of additional or alternative tasks, the tasks need not be performed in the illustrated order and/or the tasks may be performed concurrently, and/or the performance model development process 700 may be incorporated into a more comprehensive procedure or process having additional functionality not described in detail herein. Moreover, one or more of the tasks shown and described in the context of FIG. 7 could be omitted from a practical embodiment of the performance model development process 700 as long as the intended overall functionality remains intact.

In the illustrated embodiment, the performance model development process 700 obtains patient data for a number of different patients, obtains one or more sets of calibrated measurement parameters and corresponding reference measurement values for each patient, and maintains the association between an individual patient's patient data, calibrated measurement parameters, and reference measurement values (tasks 702, 704, 706, 708). In exemplary embodiments, the patient data includes one or more of the patient's age, gender, height, weight, body mass index (BMI), demographic data, and/or other parameters characterizing the patient. For each patient, at least one set of calibrated measurement parameters (e.g., output electrical current measurement, EIS values, and the like) is also obtained and maintained in association with a contemporaneous and/or corresponding reference measurement value for the physiological condition of the patient. For example, for a fingerstick or other reference blood glucose measurement for the patient, the contemporaneous or current calibrated measurement parameters output by an interstitial sensing arrangement 104, 200 may be stored or otherwise maintained in association with the reference blood glucose measurement for developing a model for calculating or otherwise predicting a blood glucose measurement as a function of one or more of the calibrated measurement parameters.

The performance model development process 700 continues by calculating or otherwise determining a model for calculating or otherwise determining a measurement value as a function of the patient data and one or more calibration measurement parameters (task 710). For example, machine learning may be utilized to determine which combination of patient data parameters and calibration measurement parameters are correlated to or predictive of the reference blood glucose measurement values, and then determine a corresponding equation, function, or model for calculating a blood glucose measurement value based on that set of input variables. Thus, the sensor performance model is capable of characterizing or mapping a particular combination of patient data and calibrated measurement parameters to a blood glucose measurement value that is effectively calibrated without requiring a fingerstick or other reference measurement to calibrate instances of the sensing arrangement 104, 200. Depending on the embodiment, the sensor performance model may be stored at the sensing arrangement 104, 200 (e.g., in memory 206) or at another remote device or database.

In exemplary embodiments, the time (or timestamps) associated with the patient data parameters and calibration measurement parameters may also be utilized as an input to the sensor performance model. For example, outputs from the sensing arrangement 104, 200 may be timestamped to allow for determination of the elapsed time since sensor insertion, time of day, or other temporal variable, which, in turn may be utilized as an input variable correlative to the sensor performance. In this manner, the sensor performance model may account for time-dependent signal changes or variations that may be specific to a particular patient (or subset of patients), fabrication process measurement(s) and/or combinations thereof.

Figure 8:
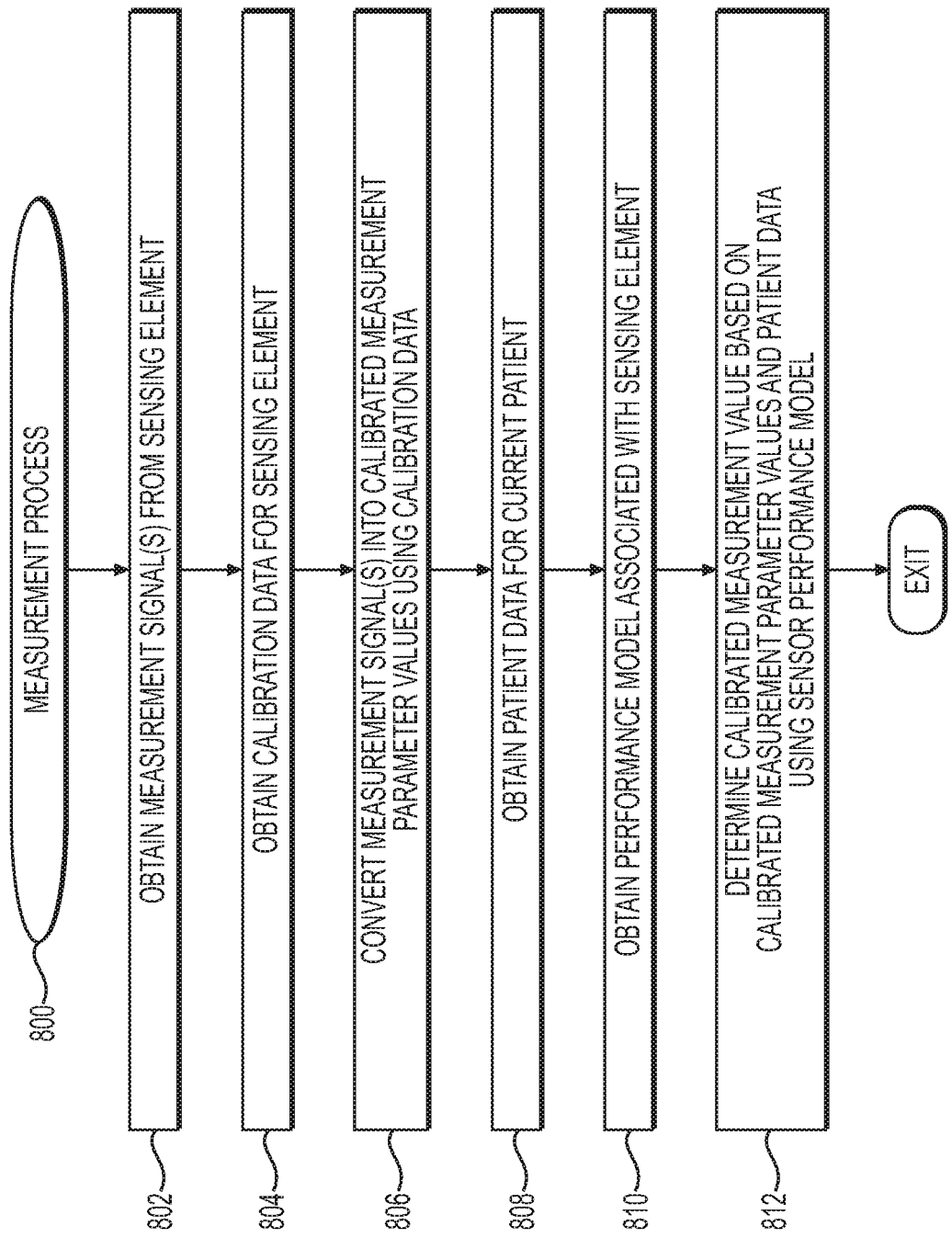
FIG. 8 is a flow diagram of an exemplary measurement process suitable for use with a sensing arrangement in conjunction with the sensor initialization process of FIG. 6 and the performance model development process of FIG. 7 in one or more exemplary embodiments.

FIG. 8 depicts an exemplary embodiment of a measurement process 800 for determining a calibrated measurement value for a physiological condition of a patient using the calibration models developed using the process 500 of FIG. 5 and the sensor performance model developed using the process 700 of FIG. 7 without requiring the patient to perform any additional calibration processes. The various tasks performed in connection with the measurement process 800 may be performed by hardware, firmware, software executed by processing circuitry, or any combination thereof. For illustrative purposes, the following description may refer to elements mentioned above in connection with FIGS. 1-3. It should be appreciated that the measurement process 800 may include any number of additional or alternative tasks, the tasks need not be performed in the illustrated order and/or the tasks may be performed concurrently, and/or the measurement process 800 may be incorporated into a more comprehensive procedure or process having additional functionality not described in detail herein. Moreover, one or more of the tasks shown and described in the context of FIG. 8 could be omitted from a practical embodiment of the measurement process 800 as long as the intended overall functionality remains intact.

The illustrated measurement process 800 begins by receiving or otherwise obtaining one or more measurement signals from a sensing element and utilizing calibration data associated with the sensing element to convert the measurement signal(s) into calibrated measurement parameters (tasks 802, 804, 806). For example, the control module 204 may sample or otherwise obtain the measurement signal(s) output by the interstitial glucose sensing element 202 that are influenced by the interstitial glucose level of the patient, and based thereon, determine raw or uncalibrated values for the output electrical current through the sensing element 202, EIS values characterizing the impedance of the sensing element 202, and the like. Thereafter, the control module 204 obtains the stored calibration factors associated with the sensing element 202 from the memory 206 and utilizes the stored calibration factors to convert the uncalibrated values into a calibrated output electrical current, calibrated EIS values, and the like.

Additionally, the measurement process 800 receives or otherwise obtains patient data associated with or otherwise characterizing the current patient and utilizes the sensor performance model to determine a calibrated measurement value using the current patient's data and the calibrated measurement parameters (tasks 808, 810, 812). For example, the patient's age, gender, height, weight, body mass index (BMI), demographic data, and/or other parameters characterizing the patient may be stored or otherwise maintained in the memory 206 of the sensing arrangement 104, 200 (or alternatively, at another device 102, 106, 108 in an infusion system 100) along with the sensor performance model associated with the type or configuration of sensing element 202 and/or sensing arrangement 104, 200 currently being utilized. The current values for the calibrated measurement parameters that have been previously identified as input variables to the sensor performance model that are correlative to calibrated measurement values are input or otherwise provided to the sensor performance model along with the subset of patient data that was previously identified as correlative to calibrated measurement values. In this manner, the control module 204 at the sensing arrangement 104, 200 (or alternatively, at another device 102, 106, 108 in an infusion system 100) utilizes the equation or function provided by the sensor performance model and its associated weightings of input variables to calculate or otherwise determine a calibrated sensor glucose measurement value based on one or more of the calibrated output electrical current, calibrated EIS values, and the like in conjunction with one or more patient data parameters. The resulting calibrated sensor glucose measurement value may then be utilized to generate corresponding dosage commands for operating the infusion device 102 or perform other actions pertaining to management of the patient's glucose levels. For example, a closed-loop operating mode utilized to control the infusion device 102 may calculate or otherwise determine a dosage command based on a difference between the calibrated sensor glucose measurement value and a target glucose value for the patient and autonomously operate a motor or other actuation arrangement of the infusion device 902 to deliver the commanded dosage of insulin to the patient.

Figure 9:
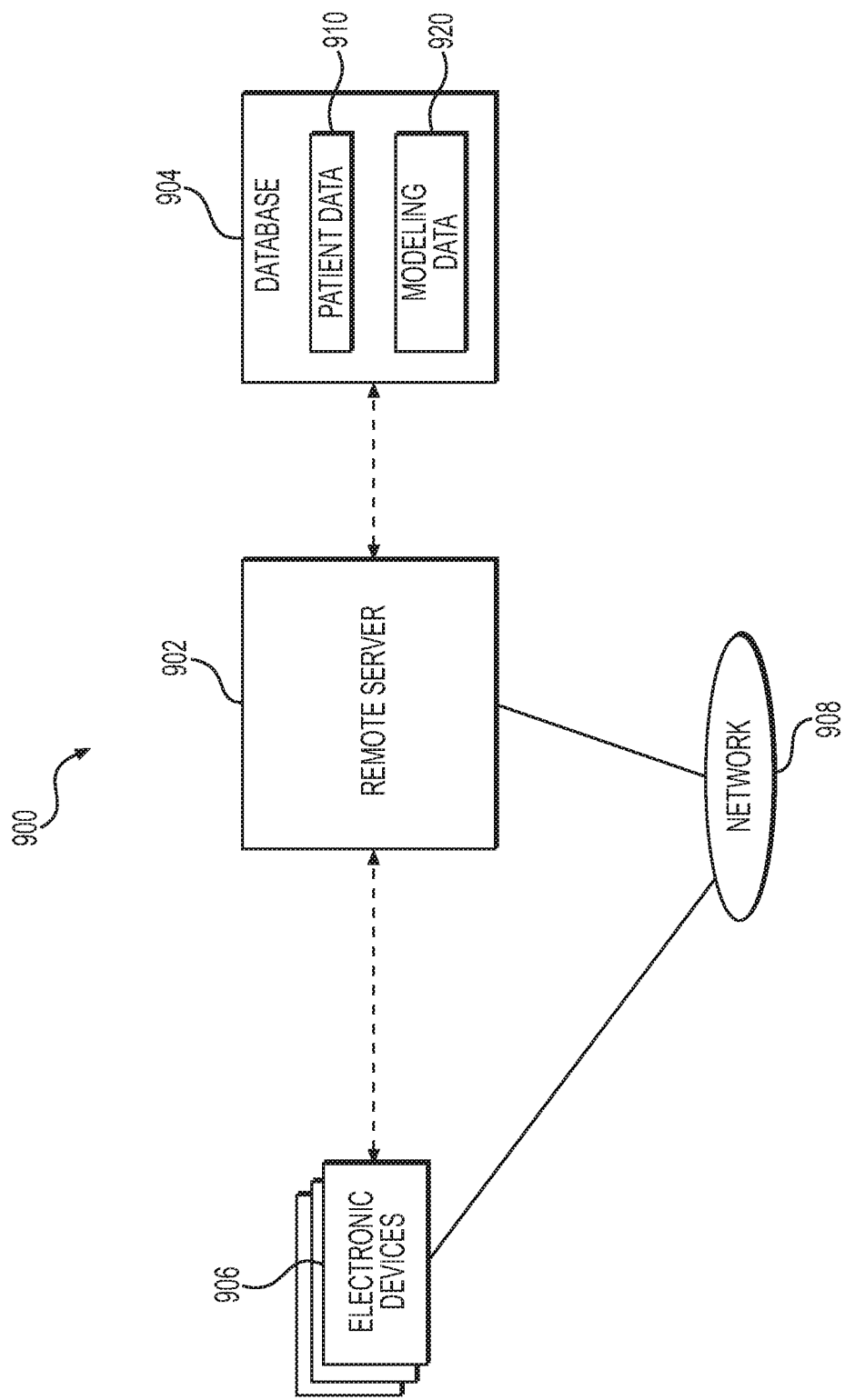
FIG. 9 is a block diagram of a data management system suitable for use with a sensing arrangement in connection with one or more of the processes of FIGS. 5-8.

FIG. 9 depicts an exemplary embodiment of a data management system 900 suitable for implementing the subject matter described herein. The data management system 900 that includes, without limitation, a computing device 902 coupled to a database 904 that is also communicatively coupled to one or more electronic devices 906 over a communications network 908, such as, for example, the Internet, a cellular network, a wide area network (WAN), or the like. It should be appreciated that FIG. 9 depicts a simplified representation of a patient data management system 900 for purposes of explanation and is not intended to limit the subject matter described herein in any way.

In exemplary embodiments, the electronic devices 906 include one or more medical devices, such as, for example, an infusion device, a sensing device, a monitoring device, and/or the like. Additionally, the electronic devices 906 may include any number of non-medical client electronic devices, such as, for example, a mobile phone, a smartphone, a tablet computer, a smart watch, or other similar mobile electronic device, or any sort of electronic device capable of communicating with the computing device 902 via the network 908, such as a laptop or notebook computer, a desktop computer, or the like. In this regard, the electronic devices 906 may also include one or more components of a process measurement system 310, a testing system 320 and/or a modeling system 330 configured to support the subject matter described herein. One or more of the electronic devices 906 may include or be coupled to a display device, such as a monitor, screen, or another conventional electronic display, capable of graphically presenting data and/or information pertaining to the physiological condition of a patient. Additionally, one or more of the electronic devices 906 also includes or is otherwise associated with a user input device, such as a keyboard, a mouse, a touchscreen, a microphone, or the like, capable of receiving input data and/or other information from a user of the electronic device 906.

In exemplary embodiments, one or more of the electronic devices 906 transmits, uploads, or otherwise provides data or information to the computing device 902 for processing at the computing device 902 and/or storage in the database 904. For example, when an electronic device 906 is realized as a sensing device, monitoring device, or other device that includes sensing element is inserted into the body of a patient or otherwise worn by the patient to obtain measurement data indicative of a physiological condition in the body of the patient, the electronic device 906 may periodically upload or otherwise transmit the measurement data to the computing device 902. In other embodiments, a client electronic device 906 may be utilized by a patient to manually define, input or otherwise provide data or information characterizing the patient and then transmit, upload, or otherwise provide such patient data to the computing device 902. In yet other embodiments, when the electronic device 906 is realized as a component of a process measurement system 310, a testing system 320 and/or a modeling system 330, the electronic device 906 may upload fabrication process measurement data, testing data, and/or other modeling data to the computing device 902 for processing at the computing device 902 and/or storage in the database 904 (e.g., modeling data 920). For example, in some embodiments, the computing device 902 may obtain the fabrication process measurement data and testing data from the process measurement system 310 and the testing system 320, respectively, and then utilize the received data to develop measurement parameter calibration factor models by or at the computing device 902 (e.g., the modeling system 330 is implemented at the computing device 902). In yet other embodiments, the computing device 902 may instead receive measurement parameter calibration factor models from the modeling system 330 for storage and/or maintenance at the database 904 for subsequent deployment to electronic devices 906.

The computing device 902 generally represents a server or other remote device configured to receive data or other information from the electronic devices 906, store or otherwise manage data in the database 904, and analyze or otherwise monitor data received from the electronic devices 906 and/or stored in the database 904. In practice, the computing device 902 may reside at a location that is physically distinct and/or separate from the electronic devices 906, such as, for example, at a facility that is owned and/or operated by or otherwise affiliated with a manufacturer of one or more medical devices utilized in connection with the patient data management system 900. For purposes of explanation, but without limitation, the computing device 902 may alternatively be referred to herein as a server, a remote server, or variants thereof. The server 902 generally includes a processing system and a data storage element (or memory) capable of storing programming instructions for execution by the processing system, that, when read and executed, cause processing system to create, generate, or otherwise facilitate the applications or software modules configured to perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof.

In exemplary embodiments, the database 904 is utilized to store or otherwise maintain historical patient data 910 for a plurality of different patients. For example, as described above, the database 904 may store or otherwise maintain reference blood glucose measurements (e.g., a fingerstick or metered blood glucose value) for different patients in association with the contemporaneous or current calibrated measurement parameters output by the respective sensing arrangement 104, 200 associated with a respective patient at or around the time of the respective blood glucose measurement. Additionally, the patient data 910 may maintain personal information associated with the different patients, including the respective patient's age, gender, height, weight, body mass index (BMI), demographic data, and/or other parameters characterizing the respective patient. In one or more embodiments, the database 904 is also utilized to store or otherwise maintain modeling data 920 that may be uploaded to and/or determined by the server 902, such as, for example, fabrication process measurement data, testing data, calibration models, and/or the like.

In one or more embodiments, the server 902 utilizes the historical patient data 910 stored in the database 904 to determine a sensor performance model for a particular type or configuration of sensing element 202 and/or sensing arrangement 104, 200 in a similar manner as described above in the context of FIG. 7. Thereafter, the server 902 may store or otherwise maintain the sensor performance model in the database 904 and subsequently provides the sensor performance model to instances of the particular type or configuration of sensing element 202 and/or sensing arrangement 104, 200. For example, upon initialization of a sensing arrangement 104, 200, 906, the control module 204 may be configured to download or otherwise obtain the appropriate sensor performance model from the remote server 902 via the network 908. Thereafter, the control module 204 may utilize the sensor performance model in conjunction with the locally stored calibration factors in memory 206 to determine calibrated glucose measurement values for the current patient without requiring a fingerstick measurement or other calibration procedure. In yet other embodiments, the sensor performance model may be provided to an infusion device 102, 906 or another electronic device 106, 108, 906 in an infusion system 100 that is configured to receive calibrated measurement parameters from the sensing arrangement 104, 200. In such embodiments, the infusion device 102, 906 or other electronic device 106, 108, 906 may utilize the obtained sensor performance model to determine calibrated glucose measurement values using calibrated measurement parameters provided by the sensing arrangement 104, 200 without requiring a fingerstick measurement or other calibration procedure.

By virtue of the subject matter described herein, individual sensing elements may be individually calibrated prior to deployment in a manner that accounts for fabrication process variations using measurement data obtained from the substrate without requiring separate testing or calibration steps after fabrication. Additionally, the calibrated measurement parameters may be utilized along with individual patient data to determine calibrated measurement values for a physiological condition of the patient without requiring the patient to perform calibration steps (e.g., obtaining fingerstick measurements, etc.). Incorporating time or other temporal variables into the sensor performance model may also account or compensate for variability or aging of interstitial glucose sensing elements with respect to time during their respective lifespans.

Performance-Based Manufacturing Controls for Manufacturing Calibration

FIG. 10 depicts an exemplary embodiment of a performance testing process 1000 suitable for use in connection with the processes described above in the context of FIG. 5-8. In this regard, the performance testing process 1000 mitigates process variation by effectively filtering or otherwise excluding instances of a sensing element that represent corner cases (or process corners) and exhibit deviation in their respective output measurement signals relative to the probable distribution of output measurement signals for that sensing element. The various tasks performed in connection with the testing process 1000 may be performed by hardware, firmware, software executed by processing circuitry, or any combination thereof. For illustrative purposes, the following description may refer to elements mentioned above in connection with FIGS. 1-3. It should be appreciated that the testing process 1000 may include any number of additional or alternative tasks, the tasks need not be performed in the illustrated order and/or the tasks may be performed concurrently, and/or the testing process 1000 may be incorporated into a more comprehensive procedure or process having additional functionality not described in detail herein. Moreover, one or more of the tasks shown and described in the context of FIG. 10 could be omitted from a practical embodiment of the testing process 1000 as long as the intended overall functionality remains intact.

Similar to the fabrication model development process 500, the illustrated testing process 1000 receives or otherwise obtains fabrication process measurements from different regions of different substrates having different instances of a sensing element fabricated thereon and receives or otherwise obtains measurement signal outputs from the different instances of sensing elements fabricated on the substrates (tasks 1002, 1004). As described above, a process measurement system 310 may analyze PCM regions 306 on a substrate 302 to obtain one or more measurements of the physical characteristics of the respective PCM region 306. The measurements of the physical characteristics of the PCM regions 306 are provided to the modeling system 330 which maintains associations between the respective measurements and the respective locations of the respective PCM regions 306 on the substrate 302. A testing system 320 then tests or otherwise analyzes the different sensing elements 304 fabricated on the substrate 302 using one or more known reference inputs to obtain, for each sensing element 304, reference measurement outputs generated or otherwise provided by the respective sensing element 304 in response to the reference input(s). For example, each sensing element 304 may be exposed to a known reference glucose concentration to obtain a corresponding output electrical current measurement, EIS value, or the like. Fabrication process measurements are assigned to each of the sensing elements, and the associations between the assigned fabrication process measurements and reference measurement outputs for each sensing element are maintained (tasks 1006, 1008), in a similar manner as described above (e.g., tasks 506, 508).

Still referring to FIG. 10, the testing process 1000 generates or otherwise determines a predictive model for a characteristic of the output measurement signal from an instance of the sensing element as a function of the fabrication process measurements based on the relationship between the reference measurement outputs and fabrication process measurements for different sensing elements (task 1010), in a similar manner as described above (e.g., task 510). In this regard, the modeling system 330 may utilize machine learning or artificial intelligence techniques to determine which combination of fabrication process measurement parameters are correlated to or predictive of the output electrical current measurement in response to a known reference glucose concentration, and then determine a corresponding equation, function, or model for calculating the magnitude, frequency, or other characteristic of the output electrical current generated by the sensing element based on that set of input fabrication process measurement variables. Thus, the model is capable of characterizing or mapping a particular combination of one or more fabrication process measurement parameters to the output measurement signal.

For example, for a number of different instances of an interstitial sensing element, each instance of the interstitial sensing element may be exposed to one or more reference glucose concentrations to obtain corresponding reference output measurement(s) (e.g., reference values for the output electrical current signal) associated with the reference glucose concentration(s). Additionally, representative fabrication process measurement values for a number of different fabrication process measurement variables (e.g., GOx thickness, GOx activity, GLM thickness, WE platinum imaginary impedance, CE platinum imaginary impedance, HSA concentration, etc.) may be obtained from or otherwise assigned to each instance of the interstitial sensing element as described above. Machine learning, artificial intelligence, or other regression techniques may then be utilized to determine an equation for calculating a predicted or expected value for the output measurement as a function of a particular combination of the fabrication process measurement variables based on the relationships between the reference output measurement(s) and the different fabrication process measurement variable values associated with the different instances of the interstitial sensing element.

Still referring to FIG. 10, after developing a predictive model calculating a measurement output generated by a sensing element as a function of input fabrication process measurement variables, the testing process 1000 continues by calculating or otherwise generating a simulated distribution of output measurements across the range of the input fabrication process measurement variables (task 1012). In this regard, the testing process 1000 calculates or otherwise determines an estimated output measurement for various combinations of values for the fabrication process measurement variables input to the predictive model. Thus, by independently varying the values for the fabrication process measurement variables input to the predictive model within their specified ranges (e.g., as dictated by the fabrication processes or other specifications), the predictive model can be utilized to extrapolate or interpolate the signal features of the sensing element within the range of fabrication possibilities.

For example, given a predictive model for calculating the output electrical current measurement as a function of the working electrode platinum imaginary impedance, GOx activity, GOx thickness, HSA concentration, and the GLM thickness, the testing process 1000 calculates a corresponding estimated output electrical current value for different combinations of working electrode platinum imaginary impedance, GOx activity, GOx thickness, HSA concentration, and the GLM thickness values from within the respective potential ranges for the working electrode platinum imaginary impedance, GOx activity, GOx thickness, HSA concentration, and the GLM thickness. In this regard, a first estimated output electrical current distribution (alternatively referred to herein as the low side simulated distribution) may be calculated for the combination of the high magnitude working electrode platinum imaginary impedance distribution, low potential GOx activity distribution, low potential GOx thickness distribution, low potential HSA concentration distribution, and the high potential GLM thickness distribution according to the fabrication processes, another estimated output electrical current distribution (alternatively referred to herein as the high side simulated distribution) may be calculated for the combination of the low magnitude working electrode platinum imaginary impedance, high potential GOx activity distribution, high potential GOx thickness distribution, high potential HSA concentration distribution, and the low potential GLM thickness distribution. The respective input variables may be individually and independently varied (e.g., using Monte Carlo techniques) around the respective end of the design range for the respective input variable to obtain a desired number of input combinations (e.g., 10,000 combinations) that are then input or otherwise provided to the predictive model to obtain a corresponding number of simulated outputs (e.g., 10,000 output samples) at the respective end of the expected output range. In this manner, the predictive model is utilized to obtain simulated or estimated output electrical current values across the full range of potential values within the two-dimensional variable space defined by the working electrode imaginary impedance, GOx activity, GOx thickness, HSA concentration, and the GLM thickness input variables. The estimated output electrical current values represent the expected distribution for the output electrical current measurement across the input variable space for the predictive model, which corresponds to the subset of fabrication process measurements (or biological, chemical, electrical, and/or physical characteristics) that are predictive of or correlative to the output electrical current measurement.

In exemplary embodiments, the testing process 1000 identifies or otherwise determines boundary or corner performance threshold values for the normal operating region for the measurement output generated by the sensing element based on the simulated distribution for measurement output derived using the predictive model (task 1014). In this regard, the boundary or threshold values represent the corner cases (or process corners) that delineate or otherwise define the normal operating range for the measurement output in response to a known reference input. The corner performance threshold or boundary values may be identified or otherwise determined based on a statistical analysis of the simulated distribution of the measurement output. In this regard, it should be noted that there are any number of different statistical techniques that may be utilized to characterize a distribution of values to define a normal operating region within the distribution, and the subject matter described herein is not limited to any particular implementation. In exemplary embodiments, the testing system 320 stores or otherwise maintains the corner threshold values defining the normal operating regions in association with the reference input value for subsequently testing the output of sensing elements in response to that reference input.

For example, a statistical mean output electrical current value may be calculated or otherwise determined based on the simulated distribution of output electrical current values, with the corner threshold output electrical current values being determined based on the standard deviation, variance, or other statistical measure of the simulated distribution of the output electrical current values relative to the mean output electrical current value. For example, the upper threshold or boundary value to be associated with a given reference input stimulus may be determined by adding three times the standard deviation of the high side simulated distribution to the mean output electrical current value responsive to that reference input for the high side simulated distribution, and the lower threshold or boundary value may be determined by subtracting three times the standard deviation of the low side simulated distribution from the mean output electrical current value of the low side simulated distribution. Thus, when a subsequent instance of the sensing element generates an output electrical current value in response to that reference input that is not within three standard deviations of the mean of either the high or low side simulated distributions, the instance of the sensing element may be discarded even though all other measurement parameters or characteristics of the instance of the sensing element are within the desired ranges. In other embodiments, the threshold or boundary values utilized to accept or reject may be different from the corner values derived from the simulated distributions, for example, by adding or subtracting some offset from the corner values. For example, the upper retention threshold may be determined by adding one and a half times the standard deviation of the high side simulated distribution to the upper corner value, which is equal to the mean output electrical current value of the high side simulated distribution plus three standard deviations of the high side simulated distribution, such that any a subsequent instance of the sensing element that generates an output electrical current value in response to the reference input that is more than four and a half standard deviations greater than the mean of the of the high side simulated distribution is discarded, while output electrical current values less than that retention threshold are retained. Thus, in such embodiments, a subsequent instance of the sensing element could generate an output electrical current value that is outside the corner boundaries from the simulated distribution but still be retained provided the output electrical current value is close enough to the corner boundary value (e.g., within one and a half standard deviations) and all other measurement parameters or characteristics of the instance of the sensing element are within the desired ranges.

In exemplary embodiments, the testing process 1000 utilizes the model-derived normal operating range performance thresholds to verify or otherwise validate the performance sensing elements after fabrication and filter or otherwise exclude non-conforming sensing elements prior to calibration and subsequent deployment (task 1016). In this regard, the testing process 1000 determines whether to accept or discard sensing elements when one or more of their output measurements in response to a known reference input is outside the respective normal operating range for that output measurement. When an instance of the sensing element generates an output measurement in response to a known stimulus that is greater than or less than a respective corner threshold value defining an upper or lower boundary of the normal operating region, the instance of the sensing element may be discarded or otherwise rejected (thereby reducing yield) without being calibrated or otherwise initialized in accordance with the sensor initialization process 600 of FIG. 6. In this regard, sensing elements or substrates may be rejected even though the fabrication process measurements are within an acceptable range. Conversely, when the output measurement is within the corner performance thresholds defining the normal operating range, the sensor initialization process 600 of FIG. 6 is performed to determine calibration factors for the sensing element.

For example, continuing the above example, if the output electrical current measurement generated by a particular sensing element in response to a reference glucose concentration is greater than or less than a corner threshold derived from the simulated distribution of output electrical current measurements across the range of potential working electrode imaginary impedance, GOx activity, GOx thickness, HSA concentration, and GLM thickness values, the sensing element may be discarded or otherwise rejected by the testing system 320, even though the working electrode imaginary impedance, GOx activity, GOx thickness, HSA concentration, and GLM thickness measurements for that sensing element are within acceptable ranges. Conversely, if the output electrical current measurement generated by the sensing element in response to the reference glucose concentration is within corner performance thresholds derived from the simulated distribution of output electrical current measurements across the range of potential working electrode imaginary impedance, GOx activity, GOx thickness, HSA concentration, and GLM thickness values, the sensing element proceeds to calibration and deployment in accordance with the sensor initialization process 600 of FIG. 6. In this regard, the working electrode imaginary impedance, GOx activity, GOx thickness, HSA concentration, and GLM thickness measurements for the sensing element may influence the calibration factors associated with the sensing element, as described above.

By virtue of controlling for manufacturing variabilities using the testing process 1000, the impact of process corners or process variations on the sensing elements may be mitigated by ensuring the sensing elements that proceed to calibration and deployment function within the normal or expected operating range for the fabrication process measurement constraints. In this manner, the performance of sensing elements may be verified or otherwise validated in addition to verifying or validating the physical, biological, chemical, and electrical characteristics prior to performing manufacturing calibration and subsequent deployment. By filtering or otherwise removing process corners or other potential performance outliers, the accuracy and reliability of the sensor initialization process 600 of FIG. 6 is improved. Additionally, in some embodiments, the testing process 1000 may be utilized to filter or otherwise remove sensing elements from the data sets that are utilized by the fabrication model development process 500 and/or the performance model development process 700, thereby improving the accuracy and reliability of the resultant models utilized by the sensor initialization process 600 and/or the measurement process 800.

For the sake of brevity, conventional techniques related to glucose sensing and/or monitoring, sampling, filtering, calibration, closed-loop glucose control, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:
1. A method of calibrating an instance of a sensing element capable of providing an electrical signal influenced by a physiological condition in a body of a user, the method comprising:
obtaining, by a first electronic device, fabrication process measurement data corresponding to measurements that were performed on a substrate having the instance of the sensing element fabricated thereon, wherein the first electronic device is configured with a calibration model or communicatively coupled to a second elec- tronic device configured with the calibration model, the calibration model being associated with the sensing element;

determining calibration data associated with the instance of the sensing element for converting the electrical signal into a calibrated measurement parameter based on the fabrication process measurement data using the calibration model, wherein determining the calibration data comprises providing, by the first electronic device, the fabrication process measurement data as input to the calibration model; and calibrating, by the first electronic device and using the calibration data, the instance of the sensing element, wherein the calibrating of the instance of the sensing element comprises storing the calibration data in a data storage element accessible to a sensing arrangement including the instance of the sensing element, and wherein the sensing arrangement uses the calibration data stored in the data storage element to convert the electrical signal into the calibrated measurement parameter.

2. The method of claim 1, wherein the calibration model calculates the calibration data based on the fabrication process measurement data.

3. The method of claim 1, wherein:
obtaining the fabrication process measurement data comprises obtaining a plurality of fabrication process measurements from a plurality of process control monitor regions on the substrate; and
determining the calibration data comprises determining the calibration data based on the plurality of fabrication process measurements.

4. The method of claim 3, further comprising determining representative fabrication process measurement data associated with the sensing element based on the plurality of fabrication process measurements, wherein determining the calibration data comprises calculating the calibration data based on the representative fabrication process measurement data by inputting the representative fabrication process measurement data to the calibration model.

5. The method of claim 4, wherein determining the representative fabrication process measurement data comprises determining the representative fabrication process measurement data based on a spatial relationship between a location of the instance of the sensing element on the substrate and respective locations of the plurality of process control monitor regions.

6. The method of claim 1, further comprising:
obtaining a plurality of fabrication process measurements from one or more substrates having a plurality of instances of the sensing element fabricated thereon;
obtaining reference measurement output from the plurality of instances of the sensing element in response to a reference input;
determining reference calibration data for the plurality of instances of the sensing element based on relationships between the reference measurement output and the reference input; and
determining the calibration model based on relationships between the plurality of fabrication process measurements and the reference calibration data.

7. The method of claim 6, the sensing element comprising an interstitial glucose sensing element, wherein obtaining the reference measurement output comprises obtaining the reference measurement output from the plurality of instances of the interstitial glucose sensing element in response to exposing each of the plurality of instances of the interstitial glucose sensing element to a reference glucose concentration.

8. The method of claim 7, wherein determining the reference calibration data comprises determining a plurality of calibration factors based on a relationship between each respective reference measurement output of a respective instance of the plurality of instances of the interstitial glucose sensing element and the reference glucose concentration.

9. The method of claim 8, further comprising determining representative fabrication process measurement data for each instance of the plurality of instances of the interstitial glucose sensing element based on a respective substrate location associated with the respective instance of the interstitial glucose sensing element relative to respective substrate locations associated with the plurality of fabrication process measurements, wherein determining the calibration model comprises determining an equation for calculating a calibration factor of the plurality of calibration factors based on relationships between the calibration factor and the representative fabrication process measurement data for each instance of the plurality of instances of the interstitial glucose sensing element.

10. The method of claim 9, wherein determining the equation comprises performing linear regression or an artificial neural network technique to produce a linear equation for calculating the calibration factor as a function of a glucose oxidase (GOx) thickness, a GOx activity, a glucose limiting membrane (GLM) thickness, a working electrode platinum imaginary impedance, a counter electrode platinum imaginary impedance, a human serum albumin (HSA) concentration, or a combination thereof.

11. The method of claim 1, wherein the sensing element comprises an interstitial glucose sensing element and the calibrated measurement parameter comprises one of a calibrated output electrical current measurement, a calibrated electrochemical impedance spectroscopy (EIS) value, and a calibrated counter electrode voltage.

12. The method of claim 1, wherein the fabrication process measurement data comprises a glucose oxidase (GOx) thickness, a GOx activity, a glucose limiting membrane (GLM) thickness, a working electrode platinum imaginary impedance, a counter electrode platinum imaginary impedance, a human serum albumin (HSA) concentration, or a combination thereof.

13. A method of calibrating an interstitial glucose sensing element, the method comprising:
obtaining, by a first electronic device, fabrication process measurement data corresponding to measurements that were performed on a substrate having an instance of the interstitial glucose sensing element fabricated thereon, wherein the first electronic device is configured with a calibration model or communicatively coupled to a second electronic device configured with the calibration model, the calibration model being associated with the interstitial glucose sensing element;
determining a calibration factor associated with the instance of the interstitial glucose sensing element for converting an uncalibrated value for a measurement parameter determined based on an output signal from the interstitial glucose sensing element into a calibrated value based on the fabrication process measurement data using the calibration model, wherein determining the calibration factor comprises providing, by the first electronic device, the fabrication process measurement data as input to the calibration model; and calibrating, by the first electronic device and using the calibration factor, the instance of the interstitial glucose sensing element, wherein the calibrating of the instance of the interstitial glucose sensing element comprises storing the calibration factor in a data storage element accessible to a sensing arrangement including the instance of the interstitial glucose sensing element, and wherein the sensing arrangement uses the calibration factor stored in the data storage element to convert the uncalibrated value into the calibrated value.

14. The method of claim 13, wherein the calibration model calculates the calibration factor based on the fabrication process measurement data.

15. The method of claim 13, wherein:
obtaining the fabrication process measurement data comprises obtaining a plurality of fabrication process measurements from a plurality of process control monitor regions on the substrate; and
determining the calibration factor comprises determining the calibration factor based on the plurality of fabrication process measurements.

16. The method of claim 15, further comprising determining representative fabrication process measurement data associated with the interstitial glucose sensing element based on the plurality of fabrication process measurements, wherein determining the calibration factor comprises calculating the calibration factor based on the representative fabrication process measurement data by inputting the representative fabrication process measurement data to the calibration model.

17. The method of claim 16, wherein determining the representative fabrication process measurement data comprises determining the representative fabrication process measurement data based on a spatial relationship between a location of the instance of the interstitial glucose sensing element on the substrate and respective locations of the plurality of process control monitor regions.

18. The method of claim 13, further comprising:
obtaining a plurality of fabrication process measurements from one or more substrates having a plurality of instances of the interstitial glucose sensing element fabricated thereon;
obtaining reference measurement output from the plurality of instances of the interstitial glucose sensing element in response to a reference input;
determining reference calibration data for the plurality of instances of the interstitial glucose sensing element based on relationships between the reference measurement output and the reference input; and
determining the calibration model based on relationships between the plurality of fabrication process measurements and the reference calibration data.

19. The method of claim 18, wherein obtaining the reference measurement output comprises obtaining the reference measurement output from the plurality of instances of the interstitial glucose sensing element in response to exposing each of the plurality of instances of the interstitial glucose sensing element to a reference glucose concentration.

20. The method of claim 19, wherein determining the reference calibration data comprises determining a plurality of calibration factors based on a relationship between each respective reference measurement output of a respective instance of the plurality of instances of the interstitial glucose sensing element and the reference glucose concentration.

* * * * *